United States Patent [19]

Nishimoto

[11] Patent Number: 5,559,209

[45] Date of Patent: Sep. 24, 1996

[54] REGULATOR REGIONS OF G PROTEINS

[75] Inventor: Ikuo Nishimoto, Brookline, Mass.

[73] Assignee: The General Hospital Corporation, Boston, Mass.

[21] Appl. No.: 19,073

[22] Filed: Feb. 18, 1993

[51] Int. Cl.$^6$ .............................. A61K 38/00; C07K 7/06; C07K 7/08; C07K 7/10
[52] U.S. Cl. ...................... 530/326; 530/327; 530/328
[58] Field of Search ................................. 530/324–326, 530/327, 328; 514/12–15

[56] References Cited

PUBLICATIONS

Okamoto et al, J. Biol. Chem. vol. 267, No. 12 pp 8342–8346. 1992.
Okamoto et al. Proc. Natl. Acad. Sci, USA, vol. 88, pp. 8020–8023, 1991.
Okamoto et al. Cell, vol. 67, 723–730, 1991. Graf et al. Mol. Pharma col. (1992), 42(5) 760–4. (see attachment).
Okamoto, et al An Intrinsic Guanine Lucleatide Exchange Inhibitor in Gi$_2$x, *J. Biological Chemistry* vol. 269, No. 19, pp 13756–13759.
Feldman et al., "Diminished B–Adrenergic Receptor Responsiveness and Cardiac Dilation in Hearts of Myopathic Syrian Hamsters (BIO 53.58) are Associated with a Funictional Abnormallity of the G Stimulatory Protein" Circulation 81:1341–1352 (1990).
Feldman et al., "Increase of the 40,000–mol wt Pertussis Toxin Substrate (G protein) in the Failing Human Heart", J. Clin. Invest. 82:189–197 (1988).
Imboden et al., "Transmembrane Signalling by the T Cell Antigen Receptor", J. Exp. Med. 161:446–456 (1985).
Nishimoto, et al, J. Bio Chem. 264: 14029–14038, 1989.
Lyons et al., *Science*, 249: 655–59, 1990.
Ui et al., Islet–Activating Protein, Pertussis Toxin: A Specific Uncoupler of Receptor–Mediated Inhibition of Adenylate Cyclase, Advances in Cyclic Nucleotide and Protein Phosphorylation Research 17:145–151, 1984.
Nishimoto et al., Possible Direct Linkage of Insulin . . . Guanine Nucleotide–binding Proteins, J. Bio. Chem., 264:14029–14038, 1989.
Okamoto et al., A Simple Structure Encodes . . . IGF–II/Mannose 6–Phosphate Receptor, Cell, 62:709–717, 1990.
Morishita et al., Isolation of Three Types of G$_1$ From Bovine Spleen$_1$, Biochem. and Biophysl. Research Comm., 172:249–255, 1990.
Lyons et al., Two G Protein Oncogenes in Human Endocrine Tumors, Science, 249:655–659, 1990.
Ignotz et al., Transforming Growth Factor–β. . . Incorporation into the Extracellular Matrix, J. Bio. Chem., 261:4337–4345, 1986.

Kurose et al., Functional Interaction of Purified Muscarinic . . . Proteins Reconstituted in Phospholipid Vesicles, J. Bio. Chem., 261:6423–6428, 1986.
Simonds et al., G$_{i2}$ mediates α$_2$–adrenergic inhibition . . . with G$_\alpha$C–terminal antibodies, Proc. Natl. Acad. Sci. USA, 86:7809–7813, 1989.
Meinkoth et al., Inhibition of Tyrotropin–induced . . . Protein of Adenylate Cyclase, G$_s$, J. Bio. Chem., 267:13239–13245, 1992.
Murray et al., Brain Somatostatin Receptor–G Protein Interaction, J. Bio. Chem., 267:2960–2965, 1992.
Okuma et al., Immunoprecipitation of α2$_a$Adrenergic . . . Protein Selective Antisera, J. Bio. Chem., 267:14826–14831, 1992.
Okamoto et al., Detection of G Protein–activator . . . Based upon Characteristics in Primary Structure, J. Bio. Chem., 267:8342–8346, 1992.
Shenker et al., The G Protein Coupled . . . Member of the Novel G Family, J. Bio. Chem., 266:9309–9313, 1991.
Okamoto et al., Indentification of a G$_s$ Activator Region . . . A–Dependent Phosphorylaion, Cell, 67:723–730, 1991.
Okamoto et al., Analysis of stimulation–G protein . . . factor II receptor peptide, Proc, Proc. Natl. Acad. Sci. USA, 88:8020–8023, 1991.
Sullivan et al., Identification of receptor contact . . . receptor–G protein coupling, Nature, 330:758–760, 1987.
Matsunaga et al., Activation of a calcium–permeable . . . II in BALB/c 3T3 cells, Am. J. Physiol., 255:C442–C446, 1988.
Kojima et al., Evidence that type II insulin–like . . . to calcium gating system, Biochem. and Biophysl. Research Comm., 154:9–19, 1988.
McClue et al., The α$_2$B adrenergic receptor . . . the guanine nucleotide binding protein, G$_i$2, Science, 269:430–434, 1990.
Rall et al., Identification of the lesion . . . the uncoupled S49 lympoma, Science, 224:365–371, 1987.
Yamashita et al., Pertussis toxin inhibits somatostatin . . . human pituitary tumor cells, Am. J. Physiol., 253:E28–E32, 1987.
Katada et al., A new GTP–binding protein . . . islet–activating protein, pertussis toxin, Science, 213:353–358, 1987.
Kaziro, ADP–ribosylating Toxins and G Proteins, pp. 189–206, 1988.

*Primary Examiner*—Elizabeth C. Weimar
*Assistant Examiner*—J. G. Marshall
*Attorney, Agent, or Firm*—Fish & Richardson P.C.

[57] ABSTRACT

A molecule having a peptide sequence of 80 or fewer amino acid residues containing the amino acid sequence of an anticouplone of any of the G proteins, which molecule is useful for inhibiting activation of the G protein by its G–coupled receptor.

14 Claims, 8 Drawing Sheets

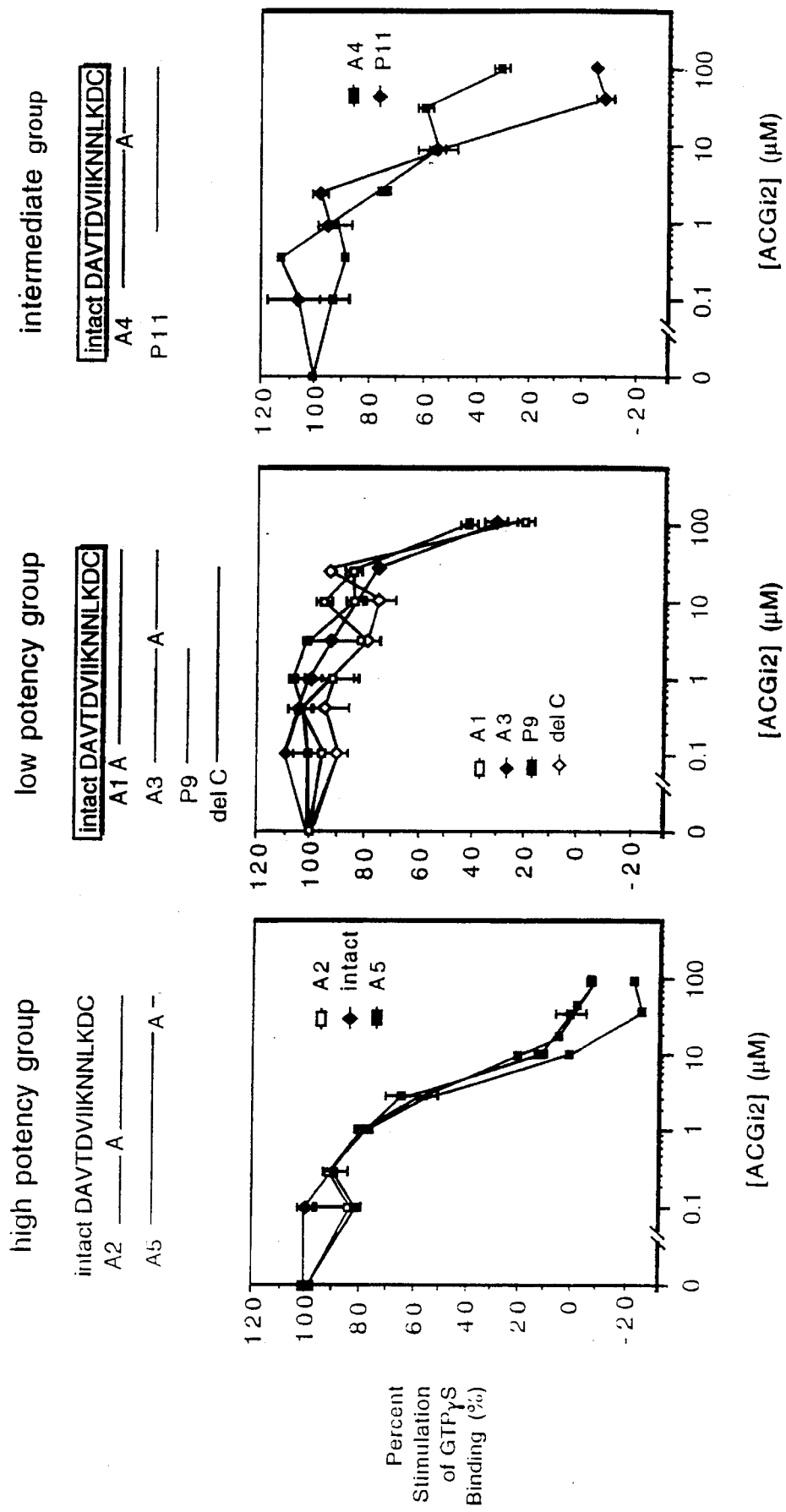

SEQUENCE LISTING ( 1 ) GENERAL INFORMATION:

( i i i ) NUMBER OF SEQUENCES: 34

( 2 ) INFORMATION FOR SEQ ID NO: 1:

( i ) SEQUENCE CHARACTERISTICS:
        ( A ) LENGTH: 15
        ( B ) TYPE: amino acid
        ( C ) STRANDEDNESS:
        ( D ) TOPOLOGY: linear ( x i ) SEQUENCE DESCRIPTION: SEQ ID NO: 1:

Asp Xaa Xaa Xaa Xaa Val Ile Ile Lys Asn Asn Leu Xaa Xaa Cys
1               5                   10                  15

( 2 ) INFORMATION FOR SEQ ID NO: 2:

( i ) SEQUENCE CHARACTERISTICS:
        ( A ) LENGTH: 15
        ( B ) TYPE: amino acid
        ( C ) STRANDEDNESS:
        ( D ) TOPOLOGY: linear ( x i ) SEQUENCE DESCRIPTION: SEQ ID NO: 2:

Asp Ala Val Thr Xaa Val Ile Ile Lys Asn Asn Leu Lys Xaa Cys
1               5                   10                  15

( 2 ) INFORMATION FOR SEQ ID NO: 3:

( i ) SEQUENCE CHARACTERISTICS:
        ( A ) LENGTH: 15
        ( B ) TYPE: amino acid
        ( C ) STRANDEDNESS:
        ( D ) TOPOLOGY: linear ( x i ) SEQUENCE DESCRIPTION: SEQ ID NO: 3:

Asp Ala Val Thr Asp Val Ile Ile Lys Asn Asn Leu Lys Asp Cys
1               5                   10                  15

( 2 ) INFORMATION FOR SEQ ID NO: 4:

( i ) SEQUENCE CHARACTERISTICS:
        ( A ) LENGTH: 24
        ( B ) TYPE: amino acid
        ( C ) STRANDEDNESS:
        ( D ) TOPOLOGY: linear ( x i ) SEQUENCE DESCRIPTION: SEQ ID NO: 4:

Asp Thr Lys Asn Val Gln Phe Val Phe Asp Ala Val Thr Asp Val Ile
1               5                   10                  15

Ile Lys Asn Asn Leu Lys Asp Cys
                20

( 2 ) INFORMATION FOR SEQ ID NO: 5:

( i ) SEQUENCE CHARACTERISTICS:
        ( A ) LENGTH: 15

(B) TYPE: amino acid
(C) STRANDEDNESS:
(D) TOPOLOGY: linear (xi) SEQUENCE DESCRIPTION: SEQ ID NO: 5:

Asp Ala Val Thr Asp Val Ile Ile Lys Asn Asn Leu Lys Glu Cys
1               5                   10                  15

(2) INFORMATION FOR SEQ ID NO: 6:

(i) SEQUENCE CHARACTERISTICS:
    (A) LENGTH: 24
    (B) TYPE: amino acid
    (C) STRANDEDNESS:
    (D) TOPOLOGY: linear (xi) SEQUENCE DESCRIPTION: SEQ ID NO: 6:

Asp Thr Lys Asn Val Gln Phe Val Phe Asp Ala Val Thr Asp Val Ile
1               5                   10                  15

Ile Lys Asn Asn Leu Lys Glu Cys
                20

(2) INFORMATION FOR SEQ ID NO: 7:

(i) SEQUENCE CHARACTERISTICS:
    (A) LENGTH: 15
    (B) TYPE: amino acid
    (C) STRANDEDNESS:
    (D) TOPOLOGY: linear (xi) SEQUENCE DESCRIPTION: SEQ ID NO: 7:

Asp Ala Val Thr Xaa Ile Ile Ile Ala Xaa Asn Leu Arg Xaa Cys
1               5                   10                  15

(2) INFORMATION FOR SEQ ID NO: 8:

(i) SEQUENCE CHARACTERISTICS:
    (A) LENGTH: 15
    (B) TYPE: amino acid
    (C) STRANDEDNESS:
    (D) TOPOLOGY: linear (xi) SEQUENCE DESCRIPTION: SEQ ID NO: 8:

Asp Ala Val Thr Asp Ile Ile Ile Ala Asn Asn Leu Arg Gly Cys
1               5                   10                  15

(2) INFORMATION FOR SEQ ID NO: 9:

(i) SEQUENCE CHARACTERISTICS:
    (A) LENGTH: 22
    (B) TYPE: amino acid
    (C) STRANDEDNESS:
    (D) TOPOLOGY: linear (xi) SEQUENCE DESCRIPTION: SEQ ID NO: 9:

Asn Asn Ile Gln Val Val Phe Asp Ala Val Thr Asp Ile Ile Ile Ala
1               5                   10                  15

Asn Asn Leu Arg Gly Cys
                20

(2) INFORMATION FOR SEQ ID NO: 10:

(i) SEQUENCE CHARACTERISTICS:
    (A) LENGTH: 15
    (B) TYPE: amino acid
    (C) STRANDEDNESS:
    (D) TOPOLOGY: linear ( x i ) SEQUENCE DESCRIPTION: SEQ ID NO: 10:

Asp Ala Val Thr Asp Ile Ile Ile Ala Lys Asn Leu Arg Gly Cys
 1               5                   10                  15

( 2 ) INFORMATION FOR SEQ ID NO: 11:

( i ) SEQUENCE CHARACTERISTICS:
        ( A ) LENGTH: 22
        ( B ) TYPE: amino acid
        ( C ) STRANDEDNESS:
        ( D ) TOPOLOGY: linear ( x i ) SEQUENCE DESCRIPTION: SEQ ID NO: 11:

Asn Asn Ile Gln Phe Val Phe Asp Ala Val Thr Asp Ile Ile Ile Ala
 1               5                   10                  15

Lys Asn Leu Arg Gly Cys
                20

( 2 ) INFORMATION FOR SEQ ID NO: 12:

( i ) SEQUENCE CHARACTERISTICS:
        ( A ) LENGTH: 15
        ( B ) TYPE: amino acid
        ( C ) STRANDEDNESS:
        ( D ) TOPOLOGY: linear ( x i ) SEQUENCE DESCRIPTION: SEQ ID NO: 12:

Asn Asp Cys Arg Asp Ile Ile Gln Arg Met His Leu Arg Gln Tyr
 1               5                   10                  15

( 2 ) INFORMATION FOR SEQ ID NO: 13:

( i ) SEQUENCE CHARACTERISTICS:
        ( A ) LENGTH: 24
        ( B ) TYPE: amino acid
        ( C ) STRANDEDNESS:
        ( D ) TOPOLOGY: linear ( x i ) SEQUENCE DESCRIPTION: SEQ ID NO: 13:

Asp Thr Glu Asn Ile Arg Arg Val Phe Asn Asp Cys Arg Asp Ile Ile
 1               5                   10                  15

Gln Arg Met His Leu Arg Gln Tyr
                20

( 2 ) INFORMATION FOR SEQ ID NO: 14:

( i ) SEQUENCE CHARACTERISTICS:
        ( A ) LENGTH: 15
        ( B ) TYPE: amino acid
        ( C ) STRANDEDNESS:
        ( D ) TOPOLOGY: linear ( x i ) SEQUENCE DESCRIPTION: SEQ ID NO: 14:

Ala Ala Val Lys Asp Thr Ile Leu Gln Leu Asn Leu Lys Glu Tyr
 1               5                   10                  15

( 2 ) INFORMATION FOR SEQ ID NO: 15:

( i ) SEQUENCE CHARACTERISTICS:
        ( A ) LENGTH: 24
        ( B ) TYPE: amino acid
        ( C ) STRANDEDNESS:
        ( D ) TOPOLOGY: linear ( x i ) SEQUENCE DESCRIPTION: SEQ ID NO: 15:

Asp Thr Glu Asn Ile Arg Phe Val Phe Ala Ala Val Lys Asp Thr Ile
 1               5                   10                  15

Leu Gln Leu Asn Leu Lys Glu Tyr
                    20

( 2 ) INFORMATION FOR SEQ ID NO: 16:

( i ) SEQUENCE CHARACTERISTICS:
        ( A ) LENGTH: 14
        ( B ) TYPE: amino acid
        ( C ) STRANDEDNESS:
        ( D ) TOPOLOGY: linear ( x i ) SEQUENCE DESCRIPTION: SEQ ID NO: 16:

Asp Ala Val Thr Asp Val Ile Ile Lys Asn Asn Leu Lys Asp
 1               5                  10

( 2 ) INFORMATION FOR SEQ ID NO: 17:

( i ) SEQUENCE CHARACTERISTICS:
        ( A ) LENGTH: 14
        ( B ) TYPE: amino acid
        ( C ) STRANDEDNESS:
        ( D ) TOPOLOGY: linear ( x i ) SEQUENCE DESCRIPTION: SEQ ID NO: 17:

Asp Ala Val Thr Asp Val Ile Ile Lys Asn Asn Leu Lys Glu
 1               5                  10

( 2 ) INFORMATION FOR SEQ ID NO: 18:

( i ) SEQUENCE CHARACTERISTICS:
        ( A ) LENGTH: 14
        ( B ) TYPE: amino acid
        ( C ) STRANDEDNESS:
        ( D ) TOPOLOGY: linear ( x i ) SEQUENCE DESCRIPTION: SEQ ID NO: 18:

Glu Ala Ala Ser Tyr Ile Gln Ser Lys Phe Glu Lys Leu Asn
 1               5                  10

( 2 ) INFORMATION FOR SEQ ID NO: 19:

( i ) SEQUENCE CHARACTERISTICS:
        ( A ) LENGTH: 10
        ( B ) TYPE: amino acid
        ( C ) STRANDEDNESS:
        ( D ) TOPOLOGY: linear ( x i ) SEQUENCE DESCRIPTION: SEQ ID NO: 19:

Lys Asn Asn Leu Lys Asp Cys Gly Leu Phe
 1               5                  10

( 2 ) INFORMATION FOR SEQ ID NO: 20:

( i ) SEQUENCE CHARACTERISTICS:
        ( A ) LENGTH: 15
        ( B ) TYPE: amino acid
        ( C ) STRANDEDNESS:
        ( D ) TOPOLOGY: linear ( x i ) SEQUENCE DESCRIPTION: SEQ ID NO: 20:

Ala Ala Val Thr Asp Val Ile Ile Lys Asn Asn Leu Lys Asp Cys
 1               5                  10                  15

( 2 ) INFORMATION FOR SEQ ID NO: 21:

( i ) SEQUENCE CHARACTERISTICS:
        ( A ) LENGTH: 15
        ( B ) TYPE: amino acid ( C ) STRANDEDNESS:
        ( D ) TOPOLOGY: linear ( x i ) SEQUENCE DESCRIPTION: SEQ ID NO: 21:

Asp Ala Val Thr Ala Val Ile Ile Lys Asn Asn Leu Lys Asp Cys
 1               5                   10                  15

( 2 ) INFORMATION FOR SEQ ID NO: 22:

( i ) SEQUENCE CHARACTERISTICS:
            ( A ) LENGTH: 15
            ( B ) TYPE: amino acid
            ( C ) STRANDEDNESS:
            ( D ) TOPOLOGY: linear ( x i ) SEQUENCE DESCRIPTION: SEQ ID NO: 22:

Asp Ala Val Thr Asp Val Ile Ile Lys Ala Asn Leu Lys Asp Cys
 1               5                   10                  15

( 2 ) INFORMATION FOR SEQ ID NO: 23:

( i ) SEQUENCE CHARACTERISTICS:
            ( A ) LENGTH: 15
            ( B ) TYPE: amino acid
            ( C ) STRANDEDNESS:
            ( D ) TOPOLOGY: linear ( x i ) SEQUENCE DESCRIPTION: SEQ ID NO: 23:

Asp Ala Val Thr Asp Val Ile Ile Lys Asn Ala Leu Lys Asp Cys
 1               5                   10                  15

( 2 ) INFORMATION FOR SEQ ID NO: 24:

( i ) SEQUENCE CHARACTERISTICS:
            ( A ) LENGTH: 15
            ( B ) TYPE: amino acid
            ( C ) STRANDEDNESS:
            ( D ) TOPOLOGY: linear ( x i ) SEQUENCE DESCRIPTION: SEQ ID NO: 24:

Asp Ala Val Thr Asp Val Ile Ile Lys Asn Asn Leu Lys Ala Cys
 1               5                   10                  15

( 2 ) INFORMATION FOR SEQ ID NO: 25:

( i ) SEQUENCE CHARACTERISTICS:
            ( A ) LENGTH: 9
            ( B ) TYPE: amino acid
            ( C ) STRANDEDNESS:
            ( D ) TOPOLOGY: linear ( x i ) SEQUENCE DESCRIPTION: SEQ ID NO: 25:

Asp Ala Val Thr Asp Val Ile Ile Lys
 1               5

( 2 ) INFORMATION FOR SEQ ID NO: 26:

( i ) SEQUENCE CHARACTERISTICS:
            ( A ) LENGTH: 11
            ( B ) TYPE: amino acid
            ( C ) STRANDEDNESS:
            ( D ) TOPOLOGY: linear ( x i ) SEQUENCE DESCRIPTION: SEQ ID NO: 26:

Asp Val Ile Ile Lys Asn Asn Leu Lys Asp Cys
 1               5                   10

( 2 ) INFORMATION FOR SEQ ID NO: 27:

( i ) SEQUENCE CHARACTERISTICS:
            ( A ) LENGTH: 14
            ( B ) TYPE: amino acid
            ( C ) STRANDEDNESS:
            ( D ) TOPOLOGY: linear ( x i ) SEQUENCE DESCRIPTION: SEQ ID NO: 27:

Arg Val Gly Leu Val Arg Gly Glu Lys Ala Arg Lys Gly Lys
 1               5                  10

( 2 ) INFORMATION FOR SEQ ID NO: 28:

( i ) SEQUENCE CHARACTERISTICS:
            ( A ) LENGTH: 25
            ( B ) TYPE: amino acid
            ( C ) STRANDEDNESS:
            ( D ) TOPOLOGY: linear ( x i ) SEQUENCE DESCRIPTION: SEQ ID NO: 28:

Leu Thr Ala Cys Leu Leu Thr Leu Leu Leu Tyr Arg Val Gly Leu Val
 1               5                  10                      15
Arg Gly Glu Lys Ala Arg Lys Gly Lys
                20              25

( 2 ) INFORMATION FOR SEQ ID NO: 29:

( i ) SEQUENCE CHARACTERISTICS:
            ( A ) LENGTH: 15
            ( B ) TYPE: amino acid
            ( C ) STRANDEDNESS:
            ( D ) TOPOLOGY: linear ( x i ) SEQUENCE DESCRIPTION: SEQ ID NO: 29:

Arg Arg Ser Ser Lys Phe Cys Leu Lys Glu His Lys Ala Leu Lys
 1               5                  10                  15

( 2 ) INFORMATION FOR SEQ ID NO: 30:

( i ) SEQUENCE CHARACTERISTICS:
            ( A ) LENGTH: 19
            ( B ) TYPE: amino acid
            ( C ) STRANDEDNESS:
            ( D ) TOPOLOGY: linear ( x i ) SEQUENCE DESCRIPTION: SEQ ID NO: 30:

Arg Asn Gln Val Arg Lys Lys Arg Gln Met Ala Ala Arg Glu Arg Lys
 1               5                  10                      15
Val Thr Arg ( 2 ) INFORMATION FOR SEQ ID NO: 31:

( i ) SEQUENCE CHARACTERISTICS:
            ( A ) LENGTH: 15
            ( B ) TYPE: amino acid
            ( C ) STRANDEDNESS:
            ( D ) TOPOLOGY: linear ( x i ) SEQUENCE DESCRIPTION: SEQ ID NO: 31:

Asp Ala Val Thr Asp Val Ile Ile Lys Asn Asn Leu Lys Xaa Cys
 1               5                  10                  15

( 2 ) INFORMATION FOR SEQ ID NO: 32:

( i ) SEQUENCE CHARACTERISTICS:
            ( A ) LENGTH: 24
            ( B ) TYPE: amino acid
            ( C ) STRANDEDNESS:

-continued (D) TOPOLOGY: linear (xi) SEQUENCE DESCRIPTION: SEQ ID NO: 32:

Asp Thr Lys Asn Val Gln Phe Val Phe Asp Ala Val Thr Asp Val Ile
 1               5                   10                  15
Ile Lys Asn Asn Leu Lys Xaa Cys
              20

(2) INFORMATION FOR SEQ ID NO: 33:

(i) SEQUENCE CHARACTERISTICS:
       (A) LENGTH: 15
       (B) TYPE: amino acid
       (C) STRANDEDNESS:
       (D) TOPOLOGY: linear (xi) SEQUENCE DESCRIPTION: SEQ ID NO: 33:

Asp Ala Val Thr Asp Ile Ile Ile Ala Xaa Asn Leu Arg Gly Cys
 1               5                   10                  15

(2) INFORMATION FOR SEQ ID NO: 34:

(i) SEQUENCE CHARACTERISTICS:
       (A) LENGTH: 22
       (B) TYPE: amino acid
       (C) STRANDEDNESS:
       (D) TOPOLOGY: linear (xi) SEQUENCE DESCRIPTION: SEQ ID NO: 34:

Asn Asn Ile Gln Xaa Val Phe Asp Ala Val Thr Asp Ile Ile Ile Ala
 1               5                   10                  15
Xaa Asn Leu Arg Gly Cys
              20

REGULATOR REGIONS OF G PROTEINS

The field of the invention is cell receptor-based signal transduction.

BACKGROUND OF THE INVENTION

Guanine nucleotide-binding proteins (G proteins) are a family of signal transducers which are found associated with the plasma membrane within eukaryotic cells, and which act to relay signals from certain cell-surface receptor molecules (G-coupled receptors) to effectors in the plasma membrane. G proteins are functional dimers consisting of $\alpha$ (G$\alpha$) and $\beta\gamma$ (G$\beta\gamma$) subunits (Stryer et al., Ann. Rev. Cell Biol. 2:391–419, 1986). Some presently-known members of this family include the G proteins termed $G_{o1}$, $G_{o2}$, $G_{i1}$, $G_{i2}$, $G_{i3}$, $G_s$, $G_q$, and the $G_q$-related family which presently includes $G_{11}$, $G_{12}$, $G_{13}$, $G_{14}$, $G_{15}$, and $G_{16}$ (see, e.g., Kaziro, "Structures of the Genes Coding for the $\alpha$ Subunits of G Proteins", Chapter 11 in *ADP—ribosylating Toxins and G Proteins* (Moss, J., and Vaughan, M. eds.) pp189–206, American Society for Microbiology, Washington, D.C., 1988). Each individual G protein is characterized as such by the particular $\alpha$ subunit species (e.g., $G_{o1}\alpha$, $G_{o2}\alpha$, etc.) which forms the $\alpha$ portion of the dimeric protein. In their unstimulated condition, G proteins are $\alpha\beta\gamma$ forms bound to guanosine diphosphate (GDP); upon receptor stimulation they dissociate into GTP-bound G$\alpha$ and nucleotide-free G$\beta\gamma$, leading to the activation of the next effector protein in the cascade. In at least one case, this activation results in the opening of a calcium channel in the membrane, thereby increasing calcium influx in the cell (Kojima et al., Biochem. Biophys. Res. Commun. 154:9–19, 1988; Matsunaga et al., Am. J. Physiol. 255:C442–C446, 1988).

Okamoto et al. (Cell 62:709–717, 1990; hereby incorporated by reference) identified the region of one G-coupled receptor protein (insulin-like growth factor II receptor, or IGF-IIR) which directly interacts with and activates $G_{i2}$; this region of IGF-IIR is sometimes referred to as that receptor's "couplone". A synthetic peptide (termed "Peptide 14") having a sequence identical to that of IGF-IIR's couplone was found to bind to and activate $G_{i2}$. Studies on synthetic variants of this peptide permitted Okamoto et al. to posit a critical peptide length (10 to 17 residues) and a motif for the couplone: two B's at the amino terminus of the peptide, and B-B-X-S or B-B-X-X-B at the carboxy terminus, where S is a basic amino acid (Lys, Arg, or His) and X is any nonbasic amino acid. In another G-coupled receptor, $\beta_2$-adrenergic receptor ($\beta$2AR), a $G_s$-activator region termed $\beta$III-2 has been identified in the third intracellular loop of $\beta$2AR (Okamoto et al., 1991a).

SUMMARY OF THE INVENTION

Applicants have identified the precise region on each of the known eukaryotic G proteins which interacts directly with the associated G-coupled receptor proteins. This region, termed the "anticouplone" or regulator region of the G protein, has been found to be critical to the function of the G protein, and therefore to signal transduction by the associated receptor. The invention thus encompasses a molecule of 80 or fewer amino acid residues. (preferably 50 or fewer, more preferably 40 or fewer, and most preferably 30 or fewer) containing the amino acid sequence of an anticouplone of any of the G proteins (e.g., a mammalian G protein such as $G_{o1}$, $G_{o2}$, $G_{i1}$, $G_{i2}$, $G_{i3}$, $G_q$, and $G_s$). The anticouplone region of a given G protein is located near the carboxy terminus of the G protein, from the 4th residue from the carboxy terminus at least to the 18th residue from that terminus, inclusive, and preferably to approximately the 27th residue from that terminus, inclusive. The molecule may contain an amino acid sequence defined by

DXXXXVIIKNNLXXC     (SEQ ID NO: 1), where X denotes any amino acid (up to two of which may be deleted) and the other letters represent specific amino acids according to the standard single-letter amino acid code. More preferably, the peptide sequence is defined by

DAVTXVIIKNNLKXC     (SEQ ID NO: 2).

Specific examples of such a sequence include

DAVTDVIIKNNLKDC     (SEQ ID NO: 3),

DTKNVQFVFDAVTDVIIKNNLKDC     (SEQ ID NO: 4),

DAVTDVIIKNNLKEC     (SEQ ID NO: 5), and

DTKNVQFVFDAVTDVIIKNNLKEC     (SEQ ID NO: 6).

Another version of the molecule of the invention includes the sequence

DAVTXIIIAXNLRXC     (SEQ ID NO: 7);

examples include

DAVTDIIIANNLRGC     (SEQ ID NO: 8),

NNIQVVFDAVTDIIIANNLRGC     (SEQ ID NO: 9),

DAVTDIIIAKNLRGC     (SEQ ID NO: 10), or

NNIQFVFDAVTDIIIAKNLRGC     (SEQ ID NO: 11).

Other molecules of the invention include a sequence

NDCRDIIQRMHLRQY     (SEQ ID NO: 12),

DTENIRRVFNDCRDIIQRMHLRQY     (SEQ ID NO: 13),

AAVKDTILQLNLKEY     (SEQ ID NO: 14), or

DTENIRFVFAAVKDTILQLNLKEY     (SEQ ID NO: 15).

The molecules of the invention may be employed in a method of inhibiting activation of a given G protein by a G-coupled receptor on a cell, which method includes the step of contacting the cell with, or otherwise introducing into the cell, a molecule containing the anticouplone sequence of the G protein, which molecule contains 40 or fewer amino acid residues. This method may be carried out, for example, by local or systemic administration of the appropriate peptide or modified peptide, or by introducing into the cell a nucleic acid encoding the anticouplone peptide together with all promoters and other elements necessary for expression of the peptide from the nucleic acid. Techniques for constructing such a nucleic acid and introducing it into the target cells are well known to those of ordinary skill in the art. Where the G protein of interest is $G_{i1}$, $G_{i2}$, or $G_{i3}$, the targeted receptor may be, for example, insulin-like growth factor II receptor (IGF-IIR), muscarinic acetylcholine receptor (mAChR), somatostatin receptor, $D_2$-dopamine receptor, $\alpha_2$-adrenergic receptor, adenosine receptor, thrombin receptor, TGF$\beta$ receptor, or any other receptor which is functionally coupled to one of those G proteins. Where the G protein of interest is $G_{o1}$ or $G_{o2}$, the receptor may be, for example, $\gamma$-butyric acid (GABA) receptor, somatostatin receptor, muscarinic acetylcholine receptor (mAChR), $\alpha_2$-adrenergic receptor, adenosine receptor, thrombin receptor, or TGFβ receptor. Examples of $G_s$-linked receptor include $\beta_2$-adrenergic receptor, glucagon receptor, IL-1 receptor, and $D_1$-dopamine receptor; while examples of $G_q$-linked receptors include the PTH/PTHrP receptor, calcitonin receptor, endothelin receptor, T cell receptor, angiotensin receptor, platelet activating factor receptor, and thromboxane $A_2$ receptor.

Other features and advantages of the invention will be apparent from the detailed description set forth below, and from the claims.

BRIEF DESCRIPTION OF THE DRAWINGS

FIG. 3 is a set of graphs illustrating the structure-function relationship of $ACG_{i2}$ on peptide 14-induced $G_{i2}$ activation. (A) Effect of $ACG_{i2}$ and high potency group variants. (B) Effect of low potency group variants. (C) Effect of intermediate potency group variants.

DETAILED DESCRIPTION

Figure 1A:
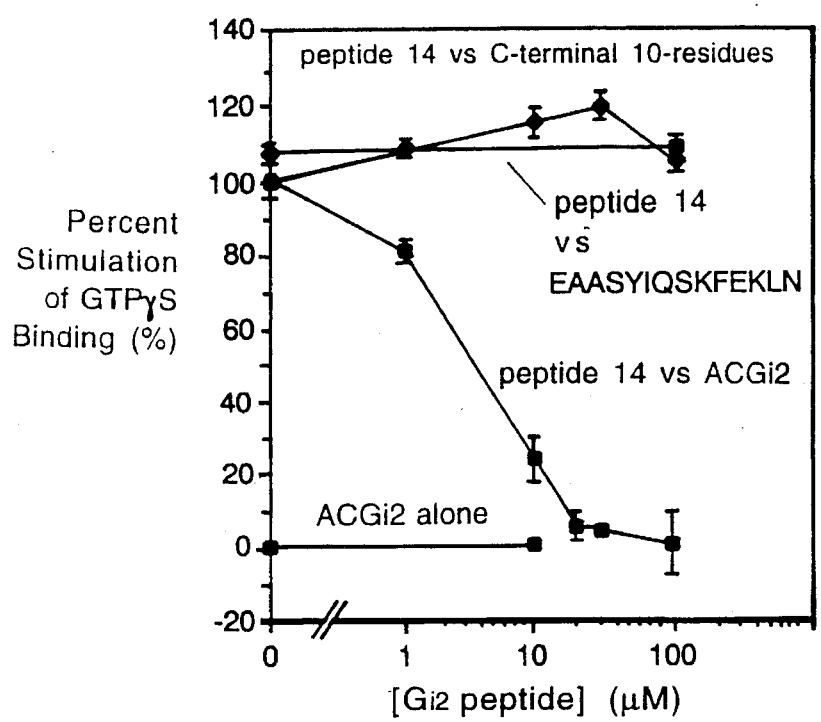
FIG. 1 is a set of graphs illustrating the effect of $ACG_{i2}$ on G protein activation. (A) Effects of $ACG_{i2}$ and control peptides on peptide 14-induced $G_{i2}$ activation. (B) Effect of $ACG_{i2}$ on TrM-peptide 14-induced $G_{i2}$ activation and βIII-2-induced $G_s$ activation. ((C) Effect of $ACG_{i2}$ on $G_{i1}$ and $G_{i3}$ activation. (D) Effect of $ACG_{i2}$ on MIII-induced $G_{i2}$ and $G_o$ activation.

The anticouplones of the invention were discovered by analyzing the sequences of the known G proteins to identify the region on each which was deemed likely to function as an anticouplone, and then testing each candidate anticouplone, and variants thereof, in appropriate in vitro and in vivo assays.

Identification of Candidate Anticouplone Sequences

On the assumption that, in order to account for the specificity of each receptor for a given type of G protein, the Gα subunit of a given G protein must participate in the direct interaction with the associated receptor's couplone, it was postulated that the anticouplone, or signal-acceptor domain, of the G protein dimer would be located, at least in part, on the Gα subunit. Certain criteria, described below, were then established to define the putative signal-acceptor domain on each G protein's α subunit. These criteria were initially applied to determine the anticouplone of $G_{i2}\alpha$, as follows: Although a recent publication suggested otherwise (Okuma et al., J. Biol. Chem. 267:14826–14831, 1992), a number of lines of evidence indicated to Applicant that at least a portion of the anticouplone sequence would be located at or near the carboxy-terminal end of the G protein (Okamoto et al., Proc. Natl. Acad. Sci. USA 88:3020–8023, 1991; Ui et al., Adv. Cyclic Nucleotide Protein Phosphorylation Res., 17:145–151, 1984; Rall et al., FEBS Lett. 224:365–371, 1987; Masters et al., Science 241:448–451, 1988; Moss and Vaughan, eds., American Society for Microbiology, 1988, pp.207–224; Simonds et al., Proc. Natl. Acad. Sci. USA, 86:7809–7813, 1989; McClue et al., FEBS Lett. 269:430–434, 1990; Shenker et al., J. Biol. Chem. 266:9309–9313, 1991; Murray-Whelan et al., J. Biol. Chem. 267:2960–2965, 1992; Meinkoth et al., J. Biol. Chem. 267:13239–13245, 1992; Okamoto and Nishimoto, Proc. Natl. Acad. Sci. USA 88:8020–8023, 1991; and Sullivan et al., Nature 330:758–760, 1987). Therefore, the first criterion specified that the candidate signal-acceptor region be located in the carboxy-terminal portion of $G_{i2}\alpha$.

Within the carboxy-terminal portion of $G_{i2}\alpha$, Applicant focused on the region Asp338–Asp351 (SEQ ID NO: 16). This region has a primary structure in which the negatively charged residues are oriented as matching the positively charged basic residues essential for the $G_{i2}$-activating function of Peptide 14. The structural determinants for this function of Peptide 14 were hypothesized to be (i) two basic residues at its amino terminus and (ii) a carboxy terminal motif of B-B-X-B or B-B-X-X-B. Asp338–Asp351 (DAVTDVIIKNNLKD) (SEQ ID NO: 16) is the only region of $G_{i2}$ that meets all of these criteria. This sequence was therefore tentatively identified as the $G_{i2}\alpha$ anticouplone. It was found that $G_{i1}\alpha$ contains the same 14 residues at a corresponding region, while $G_{i3}\alpha$ contains the almost identical sequence DAVTDVIIKNNLKE (SEQ ID NO: 17), in which the N-terminal Asp is replaced by Glu. When the four criteria are applied to $G_{o1}\alpha$ and $G_{o2}\alpha$, the resulting anticouplone sequences are defined by DAVTDIIIANNLRGC (SEQ ID NO: 8) and DAVTDIIIAKNLRGC (SEQ ID NO: 10), respectively. The anticouplone sequence of $G_s$ is NDCRDIIQRMHLRQY (SEQ ID NO: 12), while that of $G_q$ is AAVKDTILQLNLKEY (SEQ ID NO: 14).

The above reasoning was used to identify a putative receptor-binding domain on each individual Gα species. Later experiments carried out with synthetic peptides representing these putative receptor-binding domains have suggested that, rather than receptor-binding domains, these particular regions of the Gα polypeptides may serve as Gα-activating effector regions. This completely unexpected finding is discussed in detail below.

Synthesis of Anticouplone Peptides

The peptides used in this study were synthesized and purified as described (Okamoto et al., 1990; Okamoto and Nishimoto, 1991; Okamoto et al., 1991a; Okamoto and Nishimoto, 1992). The following peptides were prepared:

1. $ACG_{i2}$, corresponding both to $G_{i1}\alpha$ Asp337-Cys351 and to $G_{i2}\alpha$ Asp338-Cys352 (DAVTDVIIKNNLKDC; SEQ ID NO: 3). The fact that pertussis toxin, which catalyzes ADP-ribosylation of Cys352, attenuates $G_{i2}$ activation produced by peptide 14 (Okamoto et al., 1990, supra) as well as by IGF-IIR (Nishimoto et al., J. Biol. Chem. 264:14029–14038, 1989), prompted the inclusion of Cys352 in this peptide.

2. $ACG_{i3}$ (DAVTDVIIKNNLKEC; SEQ ID NO: 5).
3. $ACG_{o1}$ (DAVTDIIIANNLRGC; SEQ ID NO: 8).
4. $ACG_{o2}$ (DAVTDIIIAKNLRGC; SEQ ID NO: 10).
5. $ACG_q$ (NDCRDIIQRMHLRQY; SEQ ID NO: 12).
6. $ACG_q$ (AAVKDTILQLNLKEY; SEQ ID NO: 14).

7. Alternative $G_{o1}$ peptide NNIQVVFDAVTDIIIANNL-RGC (SEQ ID NO: 9).

8. Alternative $G_{o2}$ peptide NNIQFVFDAVTDIIIAKNL-RGC (SEQ ID NO: 11).

9. Alternative $G_s$ peptide DTENIRRVFNDCRDIIQRM-HLRQY (SEQ ID NO: 13).

10. Alternative $G_q$ peptide DTENIRFV-FAAVKDTILQLNLKEY (SEQ ID NO: 15).

11. Control peptide Glu297-Asp310 (EAASYIQSKFEKLN; SEQ ID NO: 18) corresponding to $G_{i2}\alpha$ Glu297-Asp310.

12. Control peptide Lys346-Phe355 (KNNLKDCGLF; SEQ ID NO: 19), representing the carboxy-terminal 10 residues of $G_{i2}\alpha$.

13. $A_1$ variant (AAVTDVIIKNNLKDC; SEQ ID NO: 20).
14. $A_2$ variant (DAVTAVIIKNNLKDC; SEQ ID NO: 21).
15. $A_3$ variant (DAVTDVIIKANLKDC; SEQ ID NO: 22).
16. $A_4$ variant (DAVTDVIIKNALKDC; SEQ ID NO: 23).
17. $A_5$ variant (DAVTDVIIKNNLKAC; SEQ ID NO: 24).
18. p9 variant (DAVTDVIIK; SEQ ID NO: 25).
19. p11 variant (DVIIKNNLKDC; SEQ ID NO: 26).
20. del C variant (DAVTDVIIKNNLKD; SEQ ID NO: 16).

21. Peptide 14 (RVGLVRGEKARKGK; SEQ ID NO: 27), the 14-residue couplone portion of the $G_{i2}$-coupled receptor protein IGF-IIR.

22. TrM peptide 14 (LTA-CLLTLLLYRVGLVRGEKARKGK; SEQ ID NO: 28), peptide 14 linked to the native transmembrane domain of IGF-IIR.

23. βIII-2 (RRSSKFCLKEHKALK; SEQ ID NO: 29), the 15-residue couplone region of the $G_s$-coupled receptor β2AR.

24. MIII peptide (RNQVRKKRQMAARERKVTR; SEQ ID NO: 30), the 19-residue couplone region of the $G_i/G_o$-coupled $M_4$ muscarinic acetylcholine receptor ($M_4$AChR).

Designed but not prepared were two additional peptides in the series:

25. Alternative $G_{i1}/G_{i2}$ peptide DTKNVQFVFDAVTD-VIIKNNLKDC (SEQ ID NO: 4), and 26. Alternative $G_{i3}$ peptide DTKNVQFVFDAVTDVI-IKNNLKEC (SEQ ID NO: 6).

In Vitro, Cell-free Assays of Anticouplone Peptides
Materials and Methods The in vitro assays described below utilize the couplone portion of each of a number of G-coupled receptors, instead of an intact receptor molecule, as a means for activating the corresponding anticouplone or intact G-protein. Except as noted below, $G_{i2}$ used in this study was trimeric $G_{i2}$ (i.e., $G_{i2}\alpha\beta\gamma$) purified from bovine brain to near homogeneity (Katada et al., FEBS Lett. 213:353–358 (1987), stored in buffer A (20 mM hepes/NaOH (pH 7.4), 1 mM EDTA, and 0.7% CHAPS), and diluted≧10 fold for assays. The $G_{i2}$ used for the reconstitution experiment was trimeric $G_{i2}$ purified from bovine spleen to homogeneity and dissolved in buffer B (Morishita et al., 1989). $G_{i3}\alpha$ (Morishita et al., Biochem. Biophys. Res. Commun. 172:249–255 (1990), was purified from bovine spleen and used in combination with 1.5-fold concentrated Gβγ (Katada et al., 1987). This preparation of $G_{i3}\alpha$ was 10–20% contaminated by $G_{i1}\alpha$, but not by other G proteins. Trimeric $G_s$ and Gβγ purified from bovine brain to near homogeneity (Katada et al., 1987) were also stored in buffer A.

mAChR (muscarinic acetylcholine receptor) was purified from porcine brain to near homogeneity (Haga et al., 1986) and dissolved in 0.5M potassium phosphate buffer (pH 7.0) containing 0.1% digitonin. This receptor preparation was reconstituted with $G_{i2}$ in phospholipid vesicles using a gel filtration method as described previously (Nishimoto et al., 1989). The concentrations of mAChR and $G_{i2}$ in the vesicles were 6.9 nM and 29 nM, respectively.

GTPγS binding Assay—GTPγS binding to G proteins was assayed at 37° C. in 20 mM Hepes/NaOH buffer (pH 7.4) containing 130 μM $MgCl_2$, 110 μM EDTA and 60 nM [$^{35}$S]GTPγS, as described previously (Okamoto et al., 1990). GTPγS binding to polypeptides was negligible. The total amount of G protein was measured as maximal GTPγS binding at room temperature, as described (Okamoto et al., Cell 67:723–730, 1991a). [$^{35}$S]GTPγS was purchased from DuPont-New England Nuclear. Binding of GTPγS to G proteins obeyed first-order kinetics according to the equation $\ln[(B_T-B)/B_T]=-k_{app}t$, where B is the binding at time t and $B_T$ is the total binding observable at an infinite time. Thus, the apparent first-order rate constant for GTPγS binding ($k_{app}$), which is equal to the slope of the tangent to the GTPγS binding curve at time 0 and represents the actual GTPγS binding rate, was calculated from this equation.

Results

In the experiment illustrated in FIG. 1A, 10 nM $G_{i2}$ was incubated with 30 μM peptide 14 (RVGLVRGEKARKGK; SEQ ID NO: 27), the couplone portion of the IGF-II receptor, in the presence of various concentrations of (□) $ACG_{i2}$ (DAVTDVIIKNNLKDC; SEQ ID NO: 3), (567) the control $G_{i2}\alpha$ Glu297-Asp310 peptide (EAASYIQSKFEKLN; SEQ ID NO: 18), or (◇) the control $G_{i2}\alpha$ Lys346-Phe355 peptide (KNNLKDCGLF; SEQ ID NO: 19) for 5 min under the GTPγS binding assay conditions described above, and GTPγS binding to G proteins was measured. The effect of $ACG_{i2}$ on $G_{i2}$ in the absence of peptide 14 is indicated by ■. Percent stimulation of GTPγS binding was calculated by subtracting the basal fractional binding and dividing by the stimulated fractional binding observed in the absence of $ACG_{i2}$. The basal fractional binding (=0%) was 0.39 mol GTPγS binding/mol $G_i/5$ min (5 $min^{-1}$). The 100% increase represents the GTPγS binding of 0.85 (5 $min^{-1}$). Values in all figures represent the mean ±S.E. of three experiments.

FIG. 1A shows that $ACG_{i2}$ peptide at 30 μM inhibits binding of GTPγS to $G_{i2}$ in the presence of peptide 14 to the basal level of binding exhibited by $G_{i2}$ in the absence of peptide 14. The $IC_{50}$ was ≈3 μM. $ACG_{i2}$ had no effect on GTPγS binding to $G_{i2}$ in the absence of peptide 14. $G_{i2}\alpha$ has another region that satisfies (I)–(III): residues Glu297-Asn310 (EAASYIQSKFEKLN; SEQ ID NO: 18). This peptide, however, showed no effect on peptide 14-induced $G_{i2}$ activation. As another control, a peptide representing the carboxy-terminal 10 residues of $G_{i2}\alpha$ (KNNLKDCGLF; SEQ ID NO: 19) was synthesized and tested in this assay. Unlike $ACG_{i2}$, this decapeptide exhibited no inhibitory effect on peptide 14-induced $G_{i2}$ activation. These findings suggest that the antagonizing effect of $ACG_{i2}$ on $G_{i2}$ activation is attributable to the specific amino acid sequence of the peptide.

Figure 1B:
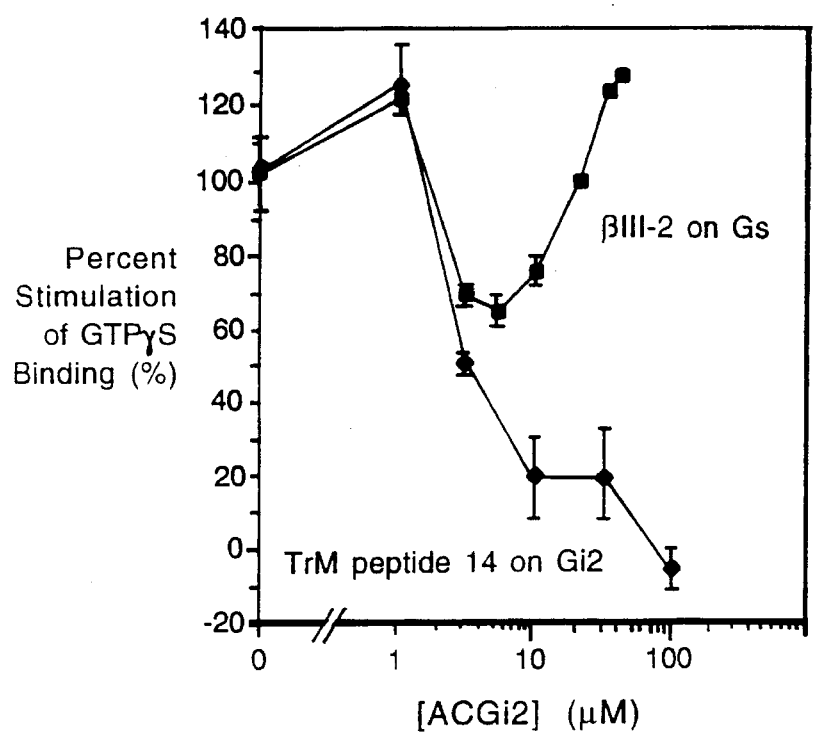

Transmembrane domain-connected peptide 14 ["TrM-peptide 14"; LTACLLTLLLYRVGLVRGEKARKGK (SEQ ID NO: 28)] is peptide 14 that is linked to the native transmembrane domain of IGF-IIR. It has been demonstrated that, in phospholipid vesicles, TrM-peptide 14 can interact with $G_{i2}$ in a manner more similar to that of the native holo receptor than can peptide 14 (Okamoto et al., 1990). In one of the experiments shown in FIG. 1B, 0.3 nM $G_{i2}$ reconstituted in phospholipid vesicles with 100 nM TrM-peptide 14 was exposed to various concentrations of $ACG_{i2}$, and GTPγS binding was measured (♦). The basal fractional GTPγS binding to $G_{i2}$ in this experiment was 0.39 (5 min$^{-1}$), and the 100% binding level was 0.88 (5 min$^{-1}$). $ACG_{i2}$ completely blocked the stimulatory effect of 100 nM TrM-peptide 14, with an $IC_{50}$ of 3 μM (FIG. 1B). Thus, even where the context more closely approximates the native environment of the G protein than in the experiment shown in FIG. 1A, $ACG_{i2}$ effectively blocks the stimulatory effect of the couplone on $G_{i2}$ with the same potency and efficacy as observed in the latter experiment.

The effect of $ACG_{i2}$ on βIII-2-induced $G_s$ activation is shown in FIG. 1B (□). GTPβS binding was measured following incubation of solubilized $G_s$ at 10 nM with 1 μM βIII-2 (RRSSKFCLKEHKALK; SEQ ID NO: 29) in the presence of $ACG_{i2}$ for 10 min. The basal fractional GTPγS binding to $G_s$ was 0.30 (10 min$^{-1}$), and 100% binding was 0.60 (10 min$^{-1}$). $ACG_{i2}$ had no effect at 1 μM. Unlike inhibition of stimulation of $G_{i2}$, which reaches 100% at 3 μM $ACG_{i2}$, the maximal inhibition of βIII-2-stimulated $G_s$ by $ACG_{i2}$ was only 40%, reflecting the fact that the $G_s$ anticouplone is not identical to $ACG_{i2}$, and so the latter peptide binds to the $G_s$-coupled receptor relatively inefficiently. At higher concentrations, $ACG_{i2}$ proved to have a positive rather than inhibitory effect on $G_s$ stimulation.

The region of $G_s\alpha$ that is comparable to the $ACG_{i2}$ region of $G_{i2}\alpha$ in topographical structure was synthesized; this region is defined by Asn384-Tyr398 of $G_s\alpha$ (NDCRDIIQRMHLRQY; SEQ ID NO: 12). At concentrations ranging up to 100 μM, this peptide ($ACG_s$) had no effect at all on peptide 14-induced $G_{i2}$ activation, again reflecting the specificity of each anticouplone (data not shown).

Figure 1C:
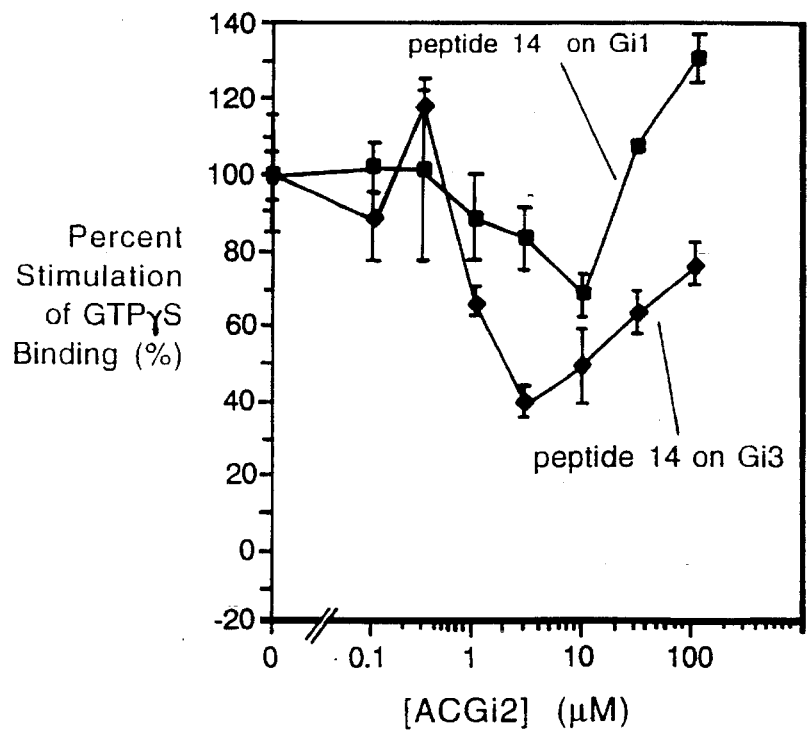

Peptide 14 is capable of activating $G_{i1}$ and $G_{i3}$ as well as $G_{i2}$ (Okamoto et al., 1990). The effect of $ACG_{i2}$ on peptide 14-induced activation of these $G_i$ proteins was examined as follows: 10 nM $G_{i1}$ (□) or $G_{i3}$ (♦) was incubated with 30 μM peptide 14 in the presence of various concentrations of $ACG_{i2}$ for 4 min, and GTPβS binding was measured. The fractional GTPγS binding to $G_{i1}$ or $G_{i3}$ at 0% was (in 4 min$^{-1}$) 0.38 or 0.30, and that at 100% was 0.54 or 0.63, respectively. Surprisingly, $ACG_{i2}$ had relatively little effect on $G_{i1}$ activation (FIG. 1C). Even high concentrations ($\geq$30 μM) of $ACG_{i2}$ maximally inhibited $G_{i1}$ activation by only 30%. The $G_{i1}$ preparation used had trace contamination by $G_o$, as described (Katada et al., FEBS Lett. 213:353–358 (1987). Since the region of $G_{i1}\alpha$ comparable to $ACG_{i2}$ has a sequence identical to $ACG_{i2}$, as mentioned above, it appears this region on $G_{i1}\alpha$ does not possess the same function as the identical region on $G_{i2}\alpha$.

FIG. 1C also shows the effect of $ACG_{i2}$ on peptide 14-induced $G_{i3}$ activation. $ACG_{i2}$ maximally inhibited $G_{i3}$ activation by ≈60%. This suggests that $ACG_{i2}$ has an antagonizing effect on $G_i$ protein activation in the order of $G_{i2}>G_{i3}>G_{i1}$. These results indicate that the $ACG_{i2}$ peptide blocks $G_{i2}$ activation in a selective manner.

Figure 1D:
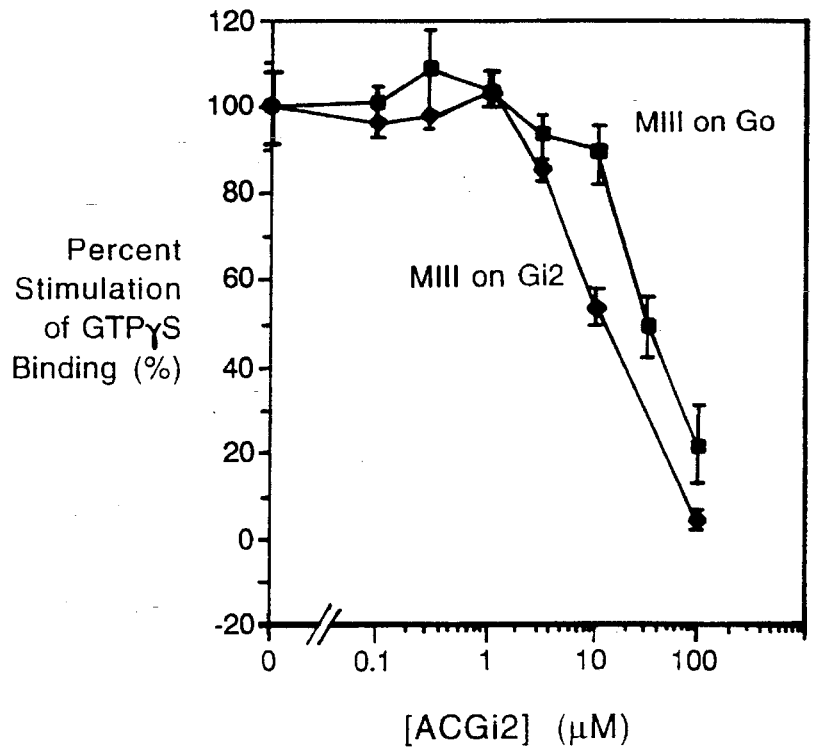

The MIII peptide is a $G_i/G_o$-activator region in the third intracellular loop of the G-coupled receptor termed $M_4$AChR (Okamoto et al., J. Biol. Chem. 267:8342–8346, 1992). This peptide has the sequence RNQVRKKRQMAARERKVTR (SEQ ID NO: 30). In the experiments illustrated in FIG. 1D, 10 nM $G_o$ (□) or $G_{i2}$ (♦) was incubated with 1 μM MIII for 2 or 5 min, respectively, and GTPγS binding was measured in the same manner as in FIG. 1A. The fractional GTPγS binding to $G_o$ at 0% and 100% was 0.36 and 0.86 (2 min$^{-1}$) respectively, and that to $G_{i2}$ at 0% and 100% was 0.30 and 0.96 (5 min$^{-1}$), respectively. MIII-induced $G_{i2}$ activation was found to be attenuated by $ACG_{i2}$ in a dose-dependent manner, with an $IC_{50}$ of 10 μM (FIG. 1D). $ACG_{i2}$ can therefore inhibit $G_{i2}$ activation caused by the effector peptides of $m_4$AChR and IGF-IIR with similar potencies. In contrast, $ACG_{i2}$ had no effect on MIII-induced $G_o$ activation at$\geq$10 μM, and its effect on MIII-induced $G_o$ activation at higher concentrations ($IC_{50}$≈30 μM) was significantly (≈3 times) less potent than its effect on MIII-induced $G_{i2}$ activation. This provides strong evidence that $ACG_{i2}$ acts on G proteins rather than on receptor peptides.

Figure 2B:
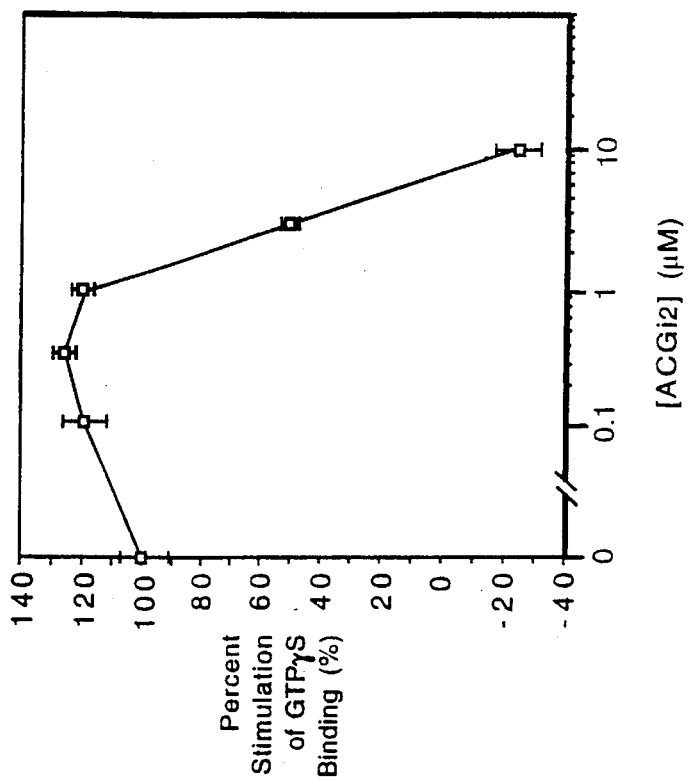
FIG. 2 is a pair of graphs illustrating the mode of action of $ACG_{i2}$. (A) Dose/response relationship of peptide 14 action in the presence of various concentrations of $ACG_{i2}$. (B) Effect of $ACG_{i2}$ on activation of 1 nM $G_{i2}$ induced by peptide 14.
Figure 2A:
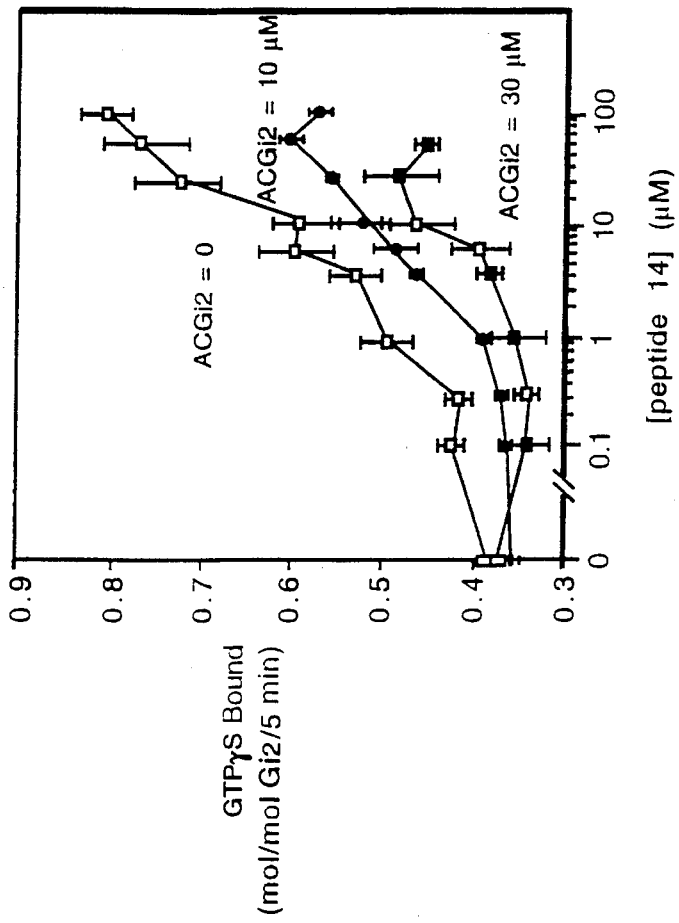

To verify the notion that $ACG_{i2}$ acts on $G_{i2}$ itself, and not on receptor sequences, two series of experiments were performed. First, the dose-response curve for peptide 14 action on $G_{i2}$ in the presence of various concentrations of $ACG_{i2}$ was generated (FIG. 2A). Following incubation of 10 nM $G_{i2}$ with various concentrations of peptide 14 in the absence (□) or presence of 10 μM (♦) or 30 μM (■) $ACG_{i2}$ for 5 min, GTPγS binding was assayed; fractional GTPγS binding to $G_{i2}$ is indicated in the figure. As the concentration of $ACG_{i2}$ increased, the efficacy of peptide 14 action was found to be decreased. This suggests that $ACG_{i2}$ does not compete with $G_{i2}$ for peptide 14.

The second series of experiments investigated the effect of $ACG_{i2}$ on lower concentrations of $G_{i2}$ that had been activated by peptide 14 to the same extent (FIG. 2B). 1 nM $G_{i2}$ was incubated for 5 min with 3 μM peptide 14 in the presence of various concentrations of $ACG_{i2}$, and GTPγS binding was measured. The fractional GTPγS binding at 0% and 100% in this experiment was 0.40 and 0.55 (5 min$^{-1}$), respectively. As shown in FIG. 2B, the $IC_{50}$ of the $ACG_{i2}$ effect on the activation of 1 nM $G_{i2}$ was ≈3 μM, which is identical to the $IC_{50}$ observed with 10 nM $G_{i2}$. If one assumes that $ACG_{i2}$ inhibits $G_{i2}$ activation by acting on receptor sequences, the antagonizing effect of $ACG_{i2}$ on smaller amounts of $G_{i2}$ at a similar intensity of peptide 14 stimulation would be observed at lower concentrations of $ACG_{i2}$, resulting in a lower $IC_{50}$. Conversely, if $ACG_{i2}$ acts on $G_{i2}$, the potency of the $ACG_{i2}$ effect on smaller compared to larger amounts of $G_{i2}$ would not be altered, because the affinity of $G_{i2}$ for $ACG_{i2}$ would presumably determine the potency of $ACG_{i2}$. Therefore, the present results suggest that $ACG_{i2}$ inhibits peptide 14/$G_{i2}$ coupling by acting on $G_{i2}$ with constant affinity.

By examining the relationship between the structure of $ACG_{i2}$ and its function in the inhibition assay described above, it was possible to determine the primary structure essential for the inhibitory action of $ACG_{i2}$. In the experiments shown in FIG. 3, $G_{i2}$ at 10 nM was incubated with 30 μM peptide 14 in the presence of various concentrations of $ACG_{i2}$ or one of its structural variants, and GTPγS binding to $G_{i2}$ was measured. The sequence of each peptide is indicated above the graphs (a bar indicates the same sequence as intact $ACG_{i2}$). The 0% and the 100% increases, which correspond to the basal and peptide 14-stimulated fractional GTPγS binding to $G_{i2}$, were similar to those described in FIG. 1A. These groups can be practically classified according to the inhibition observed at 10 μM. The high potency peptides of the first group (FIG. 3A) display$\geq$80% inhibition at 10 μM concentration; these peptides are the $A_2$ variant (DAVTAVIIKNNLKDC; SEQ ID NO: 21), in which the Asp at position five is replaced by Ala, and the $A_5$ variant (DAVTDVIIKNNLKAC; SEQ ID NO: 24), in which the Asp at position 14 is replaced by Ala. The second, low potency group (FIG. 3B) displays$\geq$30% inhibition at 10 μM, and is made up of the $A_1$ variant (AAVTDVIIKNNLKDC; SEQ ID NO: 20), in which the Asp at position 1 is replaced by Ala; the $A_3$ variant (DAVTDVIIKNNLKDC; SEQ ID NO: 22), in which the Asn at position 10 is replaced with Ala; the p9 variant (DAVTDVIIK; SEQ ID NO: 25), in which the carboxy-terminal 6 residues of $ACG_{i2}$ are deleted; and the del C variant (DAVTDVI-IKNNLKD; SEQ ID NO: 16), in which the C-terminal Cys is deleted from $ACG_{i2}$. The third, intermediate potency group (FIG. 3C) consists of the $A_4$ variant (DAVTDVI-IKNALKDC; SEQ ID NO: 23), in which the Asn at position 11 is replaced by Ala; and the p11 variant (DVIIKNNLKDC; SEQ ID NO: 26), in which the amino-terminal 4 residues are deleted.

These results suggest that the extreme amino-terminal Asp, the Asn residues at positions 10 and 11, and the carboxy-terminal Cys are essential for the inhibitory activity of $ACG_{i2}$, and that, since both the amino-terminal residue and the carboxy-terminal residue of $ACG_{i2}$ are required, the segment of $G_{i2}\alpha$ represented by $ACG_{i2}$ corresponds to the minimal anticouplone domain of $G_{i2}\alpha$. In contrast, the Glu residues at positions 2 and 14 appear to be dispensable. One can conclude from this information that, contrary to the primary hypothesis used for the initial search that anionic residues on $G_{i2}\alpha$ would interact with the basic residues of peptide 14, all of the negatively charged residues are unlikely to be oriented facing the basic residues of peptide 14 or MIII, or at least that such a matchup of anionic and basic residues is not of critical importance at some of the sites. It remains unclear how the $Cys^{352}$ residue of $ACG_{i2}$ plays a key role.

Figure 4:
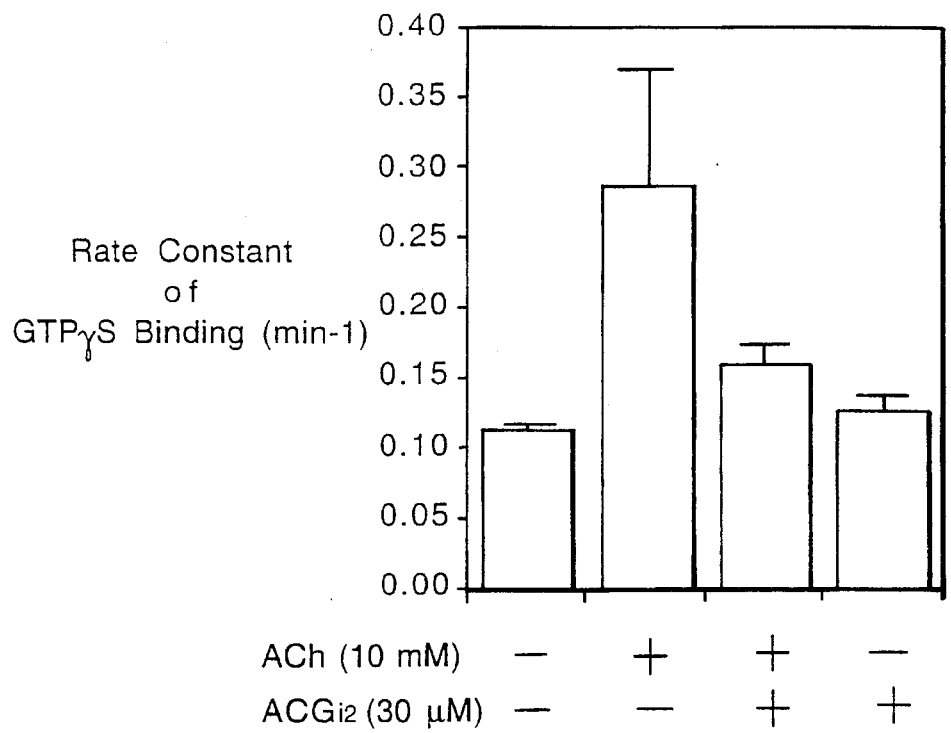
FIG. 4 is a bar graph illustrating the effect of $ACG_{i2}$ on mAChR-$G_{i2}$ coupling.

To determine whether $ACG_{i2}$ uncouples $G_{i2}$ from the signals of intact receptors as well as from the signals of their effector peptides, the effects of $ACG_{i2}$ in mAChR-$G_{i2}$ reconstituted phospholipid vesicles was studied (FIG. 4). In these vesicles, the basal value of rate constant kapp of GTPγS binding to $G_{i2}$ in the absence of acetylcholine was 0.112±0.005 (min–1); 10 mM acetylcholine (for 20 min at 30° C.) increased the $k_{app}$ value to 0.286±0.082. The magnitude of the acetylcholine effect is similar to that previously reported (Kurose et al., J. Biol. Chem. 261:6423–6428, 1986). When 10 mM acetylcholine was incubated with the vesicles in the presence of 30 μM $ACG_{i2}$, the $k_{app}$ value of GTPγS binding to $G_{i2}$ was found to be 0.157±0.013. This indicates that the $G_{i2}$ activation induced by acetylcholine in AChR-$G_{i2}$ vesicles was≈75% inhibited by $ACG_{i2}$. $ACG_{i2}$-induced inhibition was saturated at 30 μM (data not shown). $ACG_{i2}$ had no significant effect on basal $G_{i2}$ activity in the absence of acetylcholine (FIG. 4).

Figure 5:
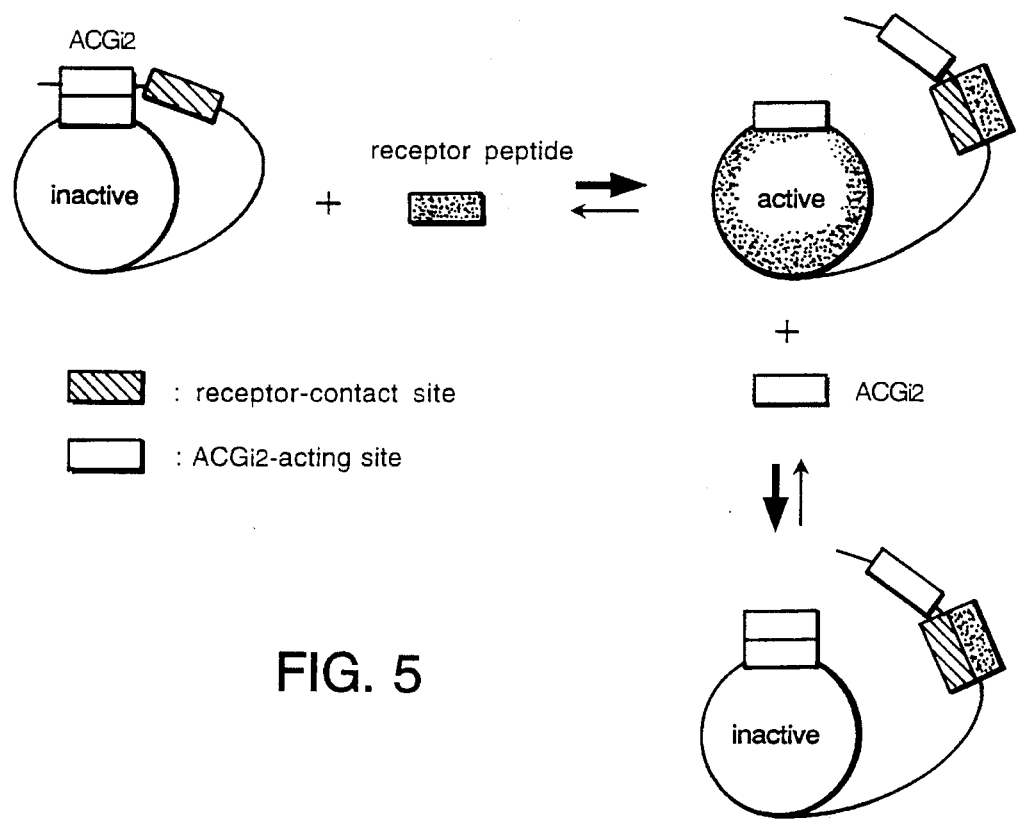
FIG. 5 is a schematic drawing illustrating a proposed mechanism whereby the activation state of $G_{i2}$ is affected by peptide 14 and/or $ACG_{i2}$ peptide.

A model illustrating the possible way in which $ACG_{i2}$ blocks the interaction of $G_{i2}$ and Peptide 14 is shown in FIG. 5. It is postulated that the anticouplone portion of $G_{i2}\alpha$ acts on a hypothetical second site of $G_{i2}\alpha$ itself, thereby stabilizing $G_{i2}\alpha$ in the unstimulated state (FIG. 5, left). Peptide 14, which has the sequence of the effector (couplone) region of IGF-IIR, binds to the contact site on $G_{i2}\alpha$, resulting in a conformational change in $G_{i2}\alpha$ that diminishes the accessibility of the anticouplone region of $G_{i2}\alpha$ to the hypothetical second site on $G_{i2}\alpha$; this leads to a decrease in binding of the two regions of $G_{i2}\alpha$ and a concomitant activation of the G protein (FIG. 5, upper right). Addition of $ACG_{i2}$ peptide causes the hypothetical second site on $G_{i2}\alpha$ to be occupied regardless of the presence or absence of Peptide 14, thereby stabilizing $G_{i2}\alpha$ in the inactive state in a manner that is independent of (and so does not compete with) $G_{i2}\alpha$ binding to Peptide 14. Although the receptor-contact site is suggested to be different than the $ACG_{i2}$ region of $G_{i2}\alpha$ in this figure, it should be emphasized that they are not necessarily different. Furthermore, it is noted that in the actual intracellular environment, there are other factors (e.g., nucleotide-binding status, GTP hydrolytic activity, and association with Gβγ) that critically affect the equilibrium of each step.

Because $ACG_{i2}$ has different effects on the various G proteins (see above), it is unlikely that the hypothetical second site resides on Gβγ (which is identical for all of the G proteins) rather than Gα (which is G-protein-specific).

Cell-based Assays

Inhibition Of somatostatin receptor function. It is known that somatostatin induces $K^+$ channel activation in a manner sensitive to pertussis toxin in human growth hormone-secreting tumors (Yamashita et al., Am. J. Physiol. 253:E28–E32, 1987). The effect of each of $ACG_{i2}$, $ACG_{i3}$, $ACG_s$, $ACG_{o1}$, and $ACG_{o2}$ on somatostatin-induced $K^+$ currents in human pituitary cells was measured using the patch clamp technique, as described below.

Three human growth hormone-secreting pituitary adenomas were obtained at transsphenoidal surgery. The tissue was minced into small pieces (less than 1 mm in diameter) and was treated with 1000 units/ml dispase (Wako, Japan). These dissociated cells (≈$10^5$ cells/ml) were seeded onto 35-mm culture dishes. The monolayer cells were cultured at 37° C. under 5% $CO_2$ in humidified air in Delbecco's modified Eagle's medium (DMEM) containing 10% heat-inactivated FCS. Electrophysiological experiments were done within 4 weeks after cell preparation.

A whole cell variation of the patch electrode voltage clamp technique was used to record membrane currents (Hamill et al., Pflüger Arch. 391:85–100, 1987). The patch electrode solution contained 95 mM potassium aspartate, 47.5 mM KCl, 1 mM $MgCl_2$, 5.0 mM EGTA (potassium salt), 10 mM HEPES/KOH (pH 7.2), 2 mM ATP and 0.1 mM GTP. One of the anticouplone peptides, dissolved in distilled water, was mixed with the patch electrode solution to a final concentration of 100 μM, and was introduced into the interior of a pituitary cell in accordance with the published method. The extracellular medium, composed of 125 mM NaCl, 5 mM KCl, 1 mM $MgCl_2$, 2.5 mM $CaCl_2$, and 10 mM HEPES/NaOH (pH 7.4), was continuously perfused around the test cell during recording, using a peristaltic pump, and $10^{-7}$M somatostatin was introduced by changing the perfused medium. The liquid junction potential between the extracellular solution and the internal solution was directly measured using a 3M KCl electrode as a reference. The value of the liquid junction potential (–8 mV) was corrected in each experiment. Glass capillaries of 1.5 mm diameter with a filament were used to fabricate an electrode for the whole cell clamp. They were coated with Sylgard and fire-polished before use. The patch electrode resistance used in these studies was in the range of 5 to 8 MΩ. The seal resistance was over several tens of GΩ. A List EPC-7 amplifier was used for the membrane current and potential. Application of voltage or current pulse, data acquisition, and analysis were done with a Gateway 2000 computer using the pCLAMP program (Axon Instruments, CA). All experiments were performed at room temperature (22°–25° C.).

The intracellular solution that filled the inside of the pipet portion of the apparatus contained one of the following anticouplone peptides at 100 μM: $ACG_{i2}$, $ACG_{i3}$, $ACG_s$, $ACG_{o1}$, or $ACG_{o2}$. The exterior of the cell was bathed with the extracellular solution containing 100 nM somatostatin while the outward $K^+$ current was monitored. In the absence of anticouplone peptides, somatostatin induces approximately 20 pA $K^+$ current over baseline. This somatostatin-induced current level is not affected by the presence of 100 μM $ACG_{i3}$, $ACG_s$, $ACG_{o1}$, or $ACG_{o2}$. $ACG_{i2}$, however, abolished the somatostatin-induced increase, in $K^+$ current, reducing the measured current to the baseline level observed in the absence of somatostatin. These data suggest that $G_{i2}$, but not $G_{i3}$, $G_s$, $G_{o1}$, or $G_{o2}$, is involved in the somatostatin receptor/K$^+$ channel linkage, and that ACG$_{i2}$ can specifically inhibit the ability of the somatostatin receptor to act on ion channels. Since this function of the somatostatin receptor on endocrine cells is related to the inhibition of hormone secretion by such cells, modulation of this receptor/G protein system by ACG$_{i2}$ permits the control of hormone secretion from endocrine cells.

Figure 6:
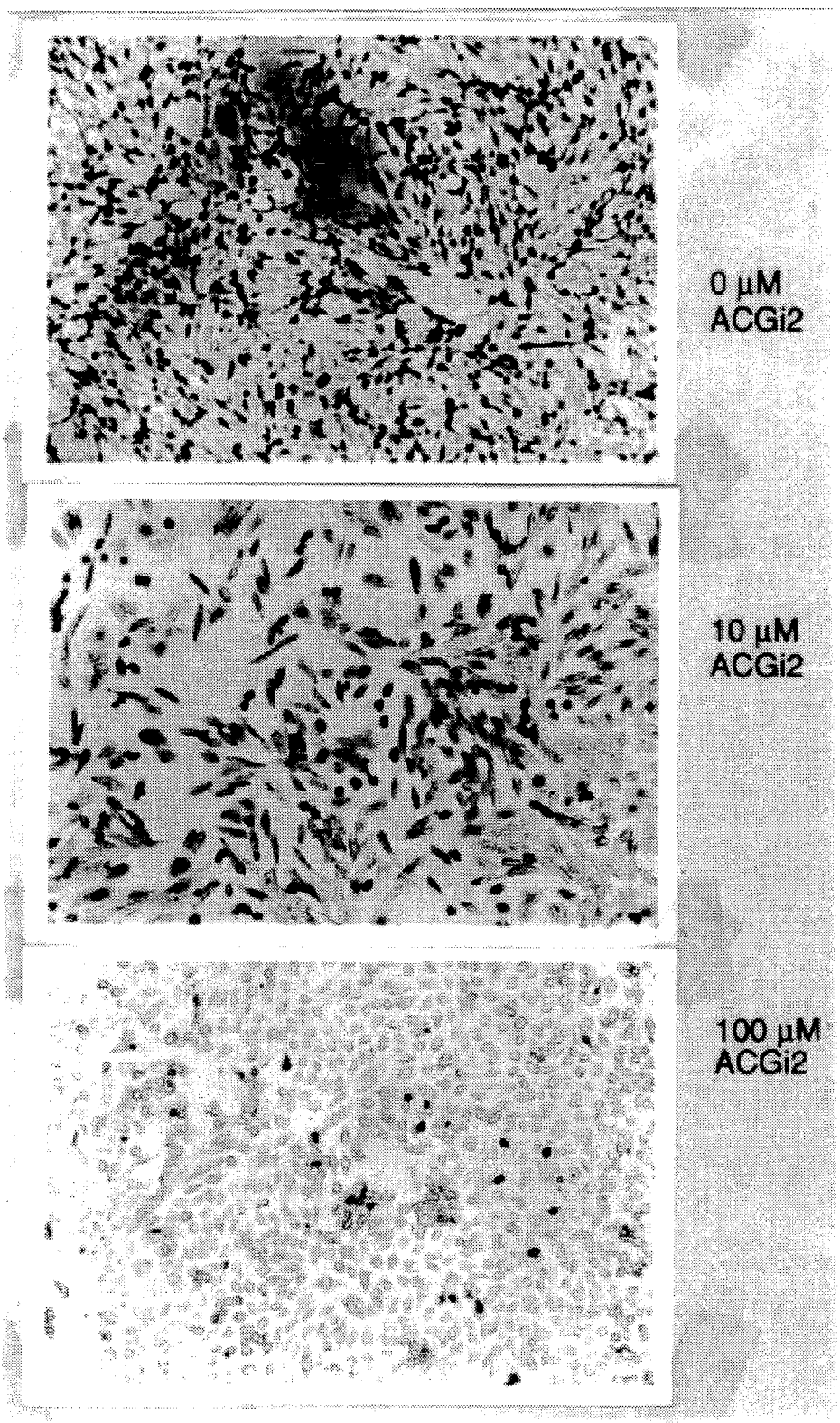
FIG. 6 is a set of three photomicrographs illustrating the inhibitory effect of $ACG_{i2}$ on serum-induced CHO cell growth.

Inhibition of cellular growth. G$_{i2}$α has been shown to be an oncogene in certain human tumors (Lyons et al, Science 249:655–659, 1990). The effect of the peptide ACG$_{i2}$ on the growth of CHO cells was measured as follows:

CHO cells were grown in Ham F12 medium (GIBCO) plus 10% fetal calf serum (FCS). Once they reached at least 80% confluency, the cells were incubated with Ham F12 plus 0.5% FCS for 24 hours. They were then incubated for an additional 24 hours with Ham F12 plus 10% FCS in the presence of BUdR and various concentrations of ACG$_{i2}$. The cells were then fixed and the BUdR incorporated into their nuclei was labeled in accordance with the instructions included with the cell proliferation detection kit (RPN.210, Amersham). FIG. 6 shows the relative extent of BUdR incorporation into cells in the presence of no ACG$_{i2}$ (top photograph), 10 μM ACG$_{i2}$ (center photograph), or 100 μM ACG$_{i2}$ (bottom photograph), wherein a labelled nucleus signifies a proliferating cell. It can be seen that FCS-induced proliferation of CHO cells is inhibited by ACG$_{i2}$ in a dose-dependent fashion, with 10 μM ACG$_{i2}$ producing significant inhibition and 100 μM inhibiting labelling almost completely. This suggests that ACG$_{i2}$ may have value as an anti-growth or anti-cancer reagent.

Inhibition of TGFβ-induced matrix formation. The secretion of matrix proteins (in particular, fibronectin) by kidney, lung and liver cells may lead to sclerosis of those organs. Transforming growth factor-β (TGFβ), which stimulates the secretion of fibronectin, may therefore contribute to such sclerosis. Since the TGFβ receptor is a G$_{o2}$-coupled receptor, the ability of ACG$_{o2}$ to inhibit the TGFβ-induced stimulation of fibronectin secretion by NRK (rat renal fibroblast) cells (Ignotz and Massagué, J. Biol. Chem. 261:4337–4345, 1986) was assayed.

Figure 7:
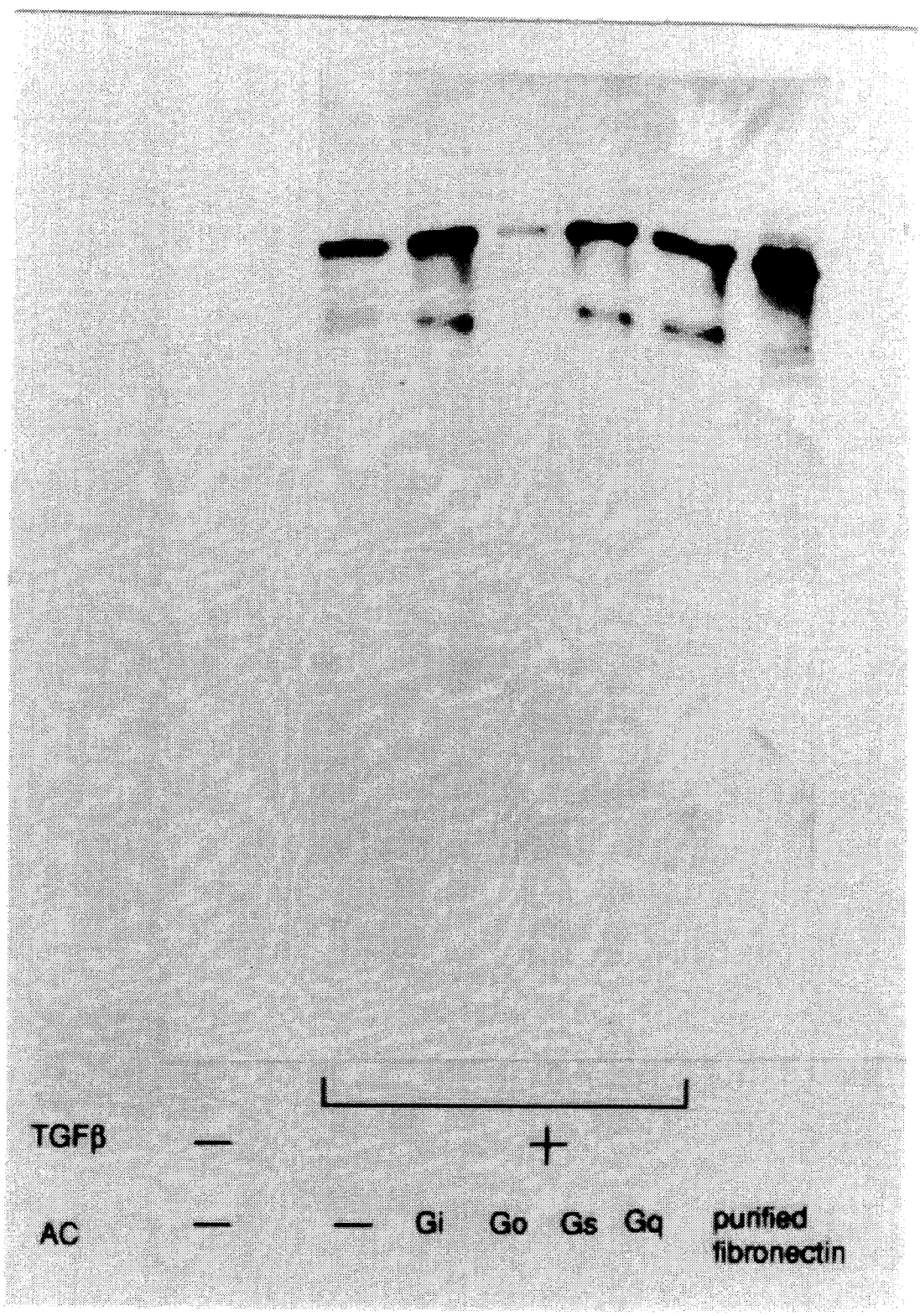
FIG. 7 is an autoradiograph of an SDS-PAGE analysis illustrating the effect of $ACG_{o2}$ on TGFβ-induced fibronectin secretion from kidney cells.

NRK cells were cultured in RPMI 1640 supplemented with 5% FCS in a CO$_2$-incubator at 37° C. The medium was replaced every two days. Cells were regularly subcultured by trypsin-EDTA before reaching confluency. In the experiments described below, the cells were grown in monolayer to confluency in 6-well culture plates (Corning, N.Y.), then incubated for 12 hours with RPMI 1640 plus 0.5% FCS, and for a further 12 hours with RPMI 1640 plus 0.5% FCS in the presence or absence of 50 pM TGFβ (R & D System, Minneapolis, Minn.), to which was added 100 μM ACG$_{i2}$, ACG$_s$, ACG$_{o2}$, or ACG$_q$. The medium from each well was collected and frozen at −20° C. until assay. Fibronectin secreted into each sample of medium was assessed by immunoblot as follows:

Each medium sample was mixed with an equal volume of 2×concentrated Laemmli buffer (Laemmli, Nature 227:680–685, 1970), and boiled at 90° C. for 5 min. Proteins were separated by electrophoresis on 7.5% SDS-polyacrylamide gel, and then transferred to a polyvinylidene difluoride sheet (Immobilon-P, Millipore) by electroelution at 0°–4° C. with constant voltage of 75 V for 8 hours. After transfer, the sheet was incubated with PBS containing 5% bovine serum albumin and 2% skim milk (Defco) overnight at room temperature to block nonspecific protein binding. The sheet was then incubated with PBS containing 0.1% bovine serum albumin and an anti-fibronectin antibody (Chemicon International, CA) at a final concentration of 0.5 mg/ml for 3 hours at room temperature. After washing with ice-cold PBS/0.05% Tween 20 three times, the sheet was incubated with 0.04 units/ml of a horseradish peroxidase-conjugated anti-rabbit IgG (Sigma, A-8257) in PBS/0.1% bovine serum albumin for 3 hours at room temperature. The sheet was washed six times with ice-cold PBS/0.05% Tween 20, incubated with ECL (Enhanced ChemiLuminescence) solution (Amersham, RPN 2101) according to instructions for 1 min, and exposed on Kodak XAR5 film for 40–60 seconds. As shown in FIG. 7, a significant amount of fibronectin is secreted by the cells exposed to TGFβ, whether or not any of ACG$_{i2}$, ACG$_s$, or ACG$_q$ is present in the culture medium. In contrast, those cells exposed to TGFβ in the presence of ACG$_{o2}$ secrete relatively little fibronectin. This indicates that ACG$_{o2}$ can inhibit the TGFβ-induced secretion of fibronectin by these cells, suggesting that ACG$_{o2}$ has use as a therapeutic for the inhibition of organosclerosis, as well as of TGFβ activity in general.

Inhibition of T cell receptor function with ACG$_q$. T cell receptor stimulation by monoclonal antibody OKT$^3$ in Jurkat cells, a line of human T cells, induces measurable polyphosphoinositide (PI) turnover. 10$^7$ cells were labelled with 5 μCi/ml [$^3$H]myoinositol in inositol-free RPMI1640 for 12 hours. After incubating the cells with 500 μM ACG$_q$, samples containing 5×10$^5$ cells were then exposed to the monoclonal antibody OKT$_3$ (Ortho) at 1:100 dilution for 5 min. Perchloric acid was added to a final concentration of 10% to lyse the cells and terminate the reaction. Cell lysates were collected into tubes and brought to pH>8 by the addition of KOH. Following centrifugation of the lysates, the supernatants were passed over a DOWX anion exchange column (Muromachi Chemicals, Japan) to separate inositol polyphosphates (IPs) from other inositol metabolites, and the amount of [$^3$H] label in the inositol trisphosphate (IP$_3$) fraction assessed. Cells exposed to OKT$_3$ incorporated [$^3$H] into IP to a level 157% that of the control cells (cells not exposed to OKT$_3$), reflecting the stimulatory effect OKT$_3$ has on PI turnover in T cells. When the cells pretreated with 500 μM ACG$_q$ were stimulated with OKT$_3$, the level of [$^3$H]incorporation into IP$_3$ was only 112% that of the unstimulated control cells; in contrast, pretreatment with 500 μM ACG$_{i2}$ did not inhibit stimulation of the cells by OKT$_3$. These results indicate that ACG$_q$, can block the function of the T cell receptor, suggesting a use of this anticouplone peptide as an immunosuppressant.

In vivo Assay of Anticouplone Peptides

Figure 8:
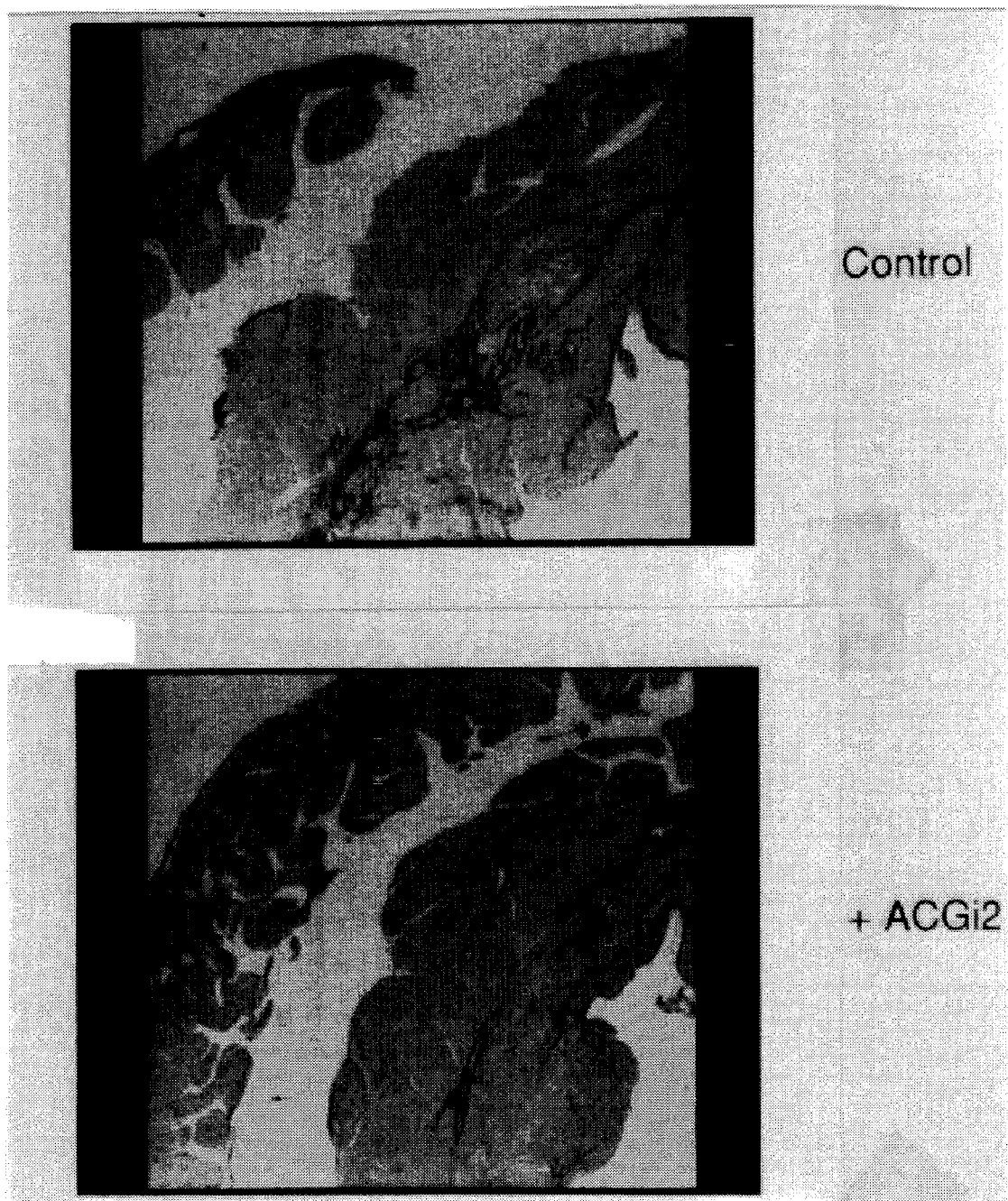
FIG. 8 is a pair of photomicrographs illustrating the effect of $ACG_{i2}$ on cardiac fibrosis in myopathic hamsters.

Myopathic syrian hamsters BIO 53.58 spontaneously develop fibrosis of the heart muscle (i.e., development of extraneous collagen fibers that eventually interfere with muscle function) by about 16 weeks of age, and as such are used as models for the human disease cardiomyopathy. In the experiment reported herein, 10-week-old BIO 53.58 hamsters received intraperitoneal injections with 5 μl of 10 mMACG$_q$, 10 mMACG$_{i2}$, or physiological saline once a week for 6 weeks. The animals were then decapitated and their hearts were excised, fixed in 10% formaldehyde solution, and cut horizontally at the level of the papillary muscle to make sections for light microscopy. The muscle sections were stained With sirius red (which specifically stains collagen), and evaluated under the microscope. In each photomicrograph shown in FIG. 8, the right ventricular free wall is located at the left of the photomicrograph and the interventricular septum is on the right. As shown in FIG. 8, top panel, the control hamsters exhibited a significant amount of heart muscle fibrosis (indicated by darkly stained lines). In contrast, the animals treated with ACG$_{i2}$ for six weeks had remarkably diminished collagen fiber formation (FIG. 8, bottom panel). Hamsters which received ACG$_q$ had undiminished, control levels of fibrosis (data not shown).

Use

Each of the anticouplone peptides of the invention may be used as a therapeutic for appropriate indications. ACG$_{i2}$ may be used where inhibition of G$_{i1}$- or G$_{i2}$-coupled receptor function is desired: for example, to treat neuromuscular diseases and cardiac arrythmia by inhibiting muscarinic acetylcholine receptors; to alleviate dwarfism by inhibiting stimulation of somatostatin receptors on pituitary cells; to block cancerous cell proliferation (or other undesired cell growth, such as cardiomyopathy) by inhibiting the G$_{i2}$ oncogene; to treat organofibrosis by inhibiting TGFβ receptors; and to treat malignant hypercalcemia by inhibiting the parathyroid/parathyroid-related protein (PTH/PTHrp) receptor. ACG$_{i3}$ would be useful for treatment of conditions related to organization and polarization of cells and cellular structures, as during organ development.

ACG$_{o1}$ will inhibit stimulation of the nerve growth factor receptor (NGFR), the activity of which is thought to affect neuronal growth. ACG$_{o2}$ is useful for inhibiting the TGFβ-induced stimulation of fibronectin secretion which leads to fibrosis and sclerosis of organs such as kidney, lung and liver. Inhibition of TGFβ is also useful in controlling the generation of cancer clones and in treating glomeronephritis. In addition, ACG$_{o2}$ can be used to prevent cancer cell growth attributable to abnormal stimulation of the cells by a mutant G$_{o2}$ oncogene.

Because G$_q$ is thought to be the G protein to which the T cell receptor is coupled, ACG$_q$ would be useful for inhibiting the function of this receptor, and thus the activation of T cells. This anticouplone therefore may be used as an immunosuppressant, such as in organ and bone marrow transplant recipients, and to treat autoimmune disease. ACG$_q$ also has potential as a treatment for AIDS, by inhibiting the abnormal signalling that results from binding of HIV gp120 to CD4 on the T cell surface. In addition, ACG$_q$, which inhibits signalling through the angiotensin receptor, may be used as a treatment for hypertension.

G$_s$-coupled receptors include the glucagon receptor, the β$_2$AR, and the PTH/PTHrP receptor. ACG$_s$ could therefore be utilized as a treatment for diabetes, hypertension, and malignant hypercalcemia. Because a mutant form of G$_s$ acts constitutively in some pituitary tumors, ACG$_s$ could be used to treat such pituitary tumor-related conditions as giantism and secondary menopause.

The treatment protocol to be used for any one of the above indications could be readily determined by one of ordinary skill in the art of pharmacology, given the teachings set forth above. The peptides of the invention may be administered by a standard method such as intravenous, intraperitoneal, intramuscular, or subcutaneous injection, and may be administered in a single dose, several doses spread over time, or a continuous infusion. The dosage will vary with the age and condition of the patient and the particular condition being treated, but is expected to be in the range of 0.5 μg/kg/day to 50 mg/kg/day. A dosage which results in a concentration at the target site of approximately 10–100 μM would be an effective dose consistent with the experimental results provided above. Incorporating the peptides into micelles or liposomes may improve delivery into cells.

OTHER EMBODIMENTS

Other embodiments are within the claims set forth below. For instance, many other receptors are known or believed to be G-coupled receptors, based in part on the their distinctive arrangement of multiple transmembrane domains known to be typical of G-coupled receptors; inappropriate signalling through these receptors can be controlled by the peptides of the invention. An example is the thyroid-stimulating hormone (TSH) receptor, overstimulation of which (e.g., by a receptor-specific antibody) leads to hyperthyroidism, or Basedow's disease. This receptor is probably a G$_s$-coupled receptor. Another example is the G protein-coupled insulin receptor, which may be overstimulated in a patient with an insulin-secreting tumor.

As described above, some amino acid residues within the defined anticouplone sequences can be replaced with other residues, with no significant loss of biological activity. For example, in ACG$_{i2}$, an Asp→Ala substitution at position 5 or 14 may be made with little or no loss of activity, while similar nonconservative substitutions at positions 1, 10, and 11 resulted in a significant loss of activity in the in vitro assay used. In general, conservative substitutions in which the relative charge of the residue occupying the substituted position does not vary (i.e., replacing an anionic residue with another anionic residue, or a hydrophobic residue with another hydrophobic residue, etc.) will have less effect on the biological activity of the resulting peptide than will nonconservative substitutions. While deletion of some residues may well not affect biological activity significantly, it is known from the work described above that the residues in both the first and the last (15th) positions of ACG$_{i2}$ are important for activity of that anticouplone. Variants of the anticouplone peptides utilized in the above experiments can be readily made by one of ordinary skill in the art of peptide synthesis, using standard methods of automated synthesis; each such peptide can then be tested in one or more of the biological assays described above. The in vitro, cell-free assays are particularly suited to testing large numbers of such peptides quickly and efficiently, permitting one to produce and evaluate hundreds of peptide variants without undue experimentation. Thus, the invention is meant to include any peptide which (a) has at least 70% sequence identity with one of the anticouplone peptides described above (preferably at least 85%), and (b) has at least 80% of the biological activity of the anticouplone peptide which it most closely resembles, in any of the biological assays described above in which that anticouplone peptide has been shown to be active. Of course, a peptide which includes the sequence of one of the anticouplones described above, plus additional sequence (including but not limited to sequence derived from the G-protein of which the anticouplone is a part), would be expected to have undiminished biological activity compared to the anticouplone itself, provided that the peptide is not too bulky or too highly charged to pass through the cellular membrane as readily as does the anticouplone peptide. Again, such longer peptides can be easily prepared and tested as described. Examples of such longer peptides are presented above as "alternative" anticouplone peptides, shown as SEQ ID NOs: 4, 6, 9, 11, 13, and 15.

Also within the invention are analogs of the above peptides, in which one or more peptide bonds have been replaced with an alternative type of covalent bond (a "peptide mimetic") which is not susceptible to cleavage by peptidases. While the in vivo results described above suggest that proteolytic degradation of the peptides following injection into the subject animal may not be a problem, it may be that for certain of the peptides, replacement of a particularly sensitive peptide bond with a noncleavable peptide mimetic will make the resulting compound more stable and thus more useful as a therapeutic. Such mimetics, and methods of incorporating them into polypeptides, are well known in the art. Similarly, the replacement of an L-amino acid residue of the anticouplone peptide with the corresponding D-amino acid residue is a standard way of rendering the polypeptide less sensitive to proteolysis. Also useful in this regard are amino-terminal blocking groups such as t-butyloxycarbonyl, acetyl, ethyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4-dinitrophenyl. Blocking the charged amino- and carboxy-termini of the peptides would have the additional benefit of enhancing passage of the peptide through the hydrophobic cellular membrane and into the cell.

What is claimed is:

1. A molecule comprising the anticouplone sequence of a G protein, wherein said molecule consists of a peptide having an amino acid sequence selected from the group consisting of

| DAVTDVIIKNNLKDC | (SEQ ID NO: 3); |
| DTKNVQFVFDAVTDVIIKNNLKDC | (SEQ ID NO: 4); |
| DAVTDVIIKNNLKEC | (SEQ ID NO: 5); |
| DTKNVQFVFDAVTDVIIKNNLKEC | (SEQ ID NO: 6); |
| DAVTDIIIANNLRGC | (SEQ ID NO: 8); |
| NNIQVVFDAVTDIIIANNLRGC | (SEQ ID NO: 9); |
| DAVTDIIIAKNLRGC | (SEQ ID NO: 10); |
| NNIQFVFDAVTDIIIAKNLRGC | (SEQ ID NO: 11); |
| NDCRDIIQRMHLRQY | (SEQ ID NO: 12); |
| DTENIRRVFNDCRDIIQRMHLRQY | (SEQ ID NO: 13); |
| AAVKDTILQLNLKEY | (SEQ ID NO: 14); and |
| DTENIRFVFAAVKDTILQLNLKEY | (SEQ ID NO: 15). |

2. The molecule of claim 1, wherein said molecule consists of a peptide having the amino acid sequence

DAVTDVIIKNNLKDC        (SEQ ID NO: 3).

3. The molecule of claim 1, wherein said molecule consists of a peptide having the amino acid sequence

DTKNVQFVFDAVTDVIIKNNLKDC        (SEQ ID NO: 4).

4. The molecule of claim 1, wherein said molecule consists of a peptide having the amino acid sequence

DAVTDVIIKNNLKEC        (SEQ ID NO: 5).

5. The molecule of claim 1, wherein said molecule consists of a peptide having the amino acid sequence

DTKNVQFVFDAVTDVIIKNNLKEC        (SEQ ID NO: 6).

6. The molecule of claim 1, wherein said molecule consists of a peptide having the amino acid sequence

DAVTDIIIANNLRGC        (SEQ ID NO: 8).

7. The molecule of claim 1, wherein said molecule consists of a peptide having the amino acid sequence

NNIQVVFDAVTDIIIANNLRGC        (SEQ ID NO: 9).

8. The molecule of claim 1, wherein said molecule consists of a peptide having the amino acid sequence

DAVTDIIIAKNLRGC        (SEQ ID NO: 10).

9. The molecule of claim 1, wherein said molecule consists of a peptide having the amino acid sequence

NNIQFVFDAVTDIIIAKNLRGC        (SEQ ID NO: 11).

10. The molecule of claim 1, wherein said molecule consists of a peptide having the amino acid sequence

NDCRDIIQRMHLRQY    (SEQ ID NO: 12).

11. The molecule of claim 1, wherein said molecule consists of a peptide having the amino acid sequence

DTENIRRVFNDCRDIIQRMHLRQY    (SEQ ID NO: 13).

12. The molecule of claim 1, wherein said molecule consists of a peptide having the amino acid sequence

AAVKDTILQLNLKEY    (SEQ ID NO: 14).

13. The molecule of claim 1, wherein said molecule consists of a peptide having the amino acid sequence

DTENIRFVFAAVKDTILQLNLKEY    (SEQ ID NO: 15).

14. A molecule consisting of a peptide having an amino acid sequence selected from the group consisting of

| | |
|---|---|
| DAVTDVIIKNNLKD | (SEQ ID NO: 16); |
| DAVTDVIIKNNLKE | (SEQ ID NO: 17); |
| AAVTDVIIKNNLKDC | (SEQ ID NO: 20); |
| DAVTAVIIKNNLKDC | (SEQ ID NO: 21); |
| DAVTDVIIKANLKDC | (SEQ ID NO: 22); |
| DAVTDVIIKNALKDC | (SEQ ID NO: 23); |
| DAVTDVIIKNNLKAC | (SEQ ID NO: 24); |
| DAVTDVIIK | (SEQ ID NO: 25); and |
| DVIIKNNLKDC | (SEQ ID NO: 26). |

* * * * *

UNITED STATES PATENT AND TRADEMARK OFFICE
CERTIFICATE OF CORRECTION

PATENT NO.   : 5,559,209

DATED        : September 24, 1996

INVENTOR(S)  : Ikuo Nishimoto

Page 1 of 3

It is certified that error appears in the above-identified patent and that said Letters Patent is hereby corrected as shown below: On the title page: Item [56] Reference Cited:

Under PUBLICATIONS

In the left column, line 5, delete "Graf et al. Mol.";

line 6, before "Pharma col.", insert --Graf et al., Mol.--; replace "Pharma col." with --Pharmacol.--; and delete "(see attachment)";

line 8, replace "Gi$_2$x" with --Gi$_2\alpha$--; and replace "*Chemistry*vol." with --*Chemistry* vol.--; and line 26, replace "Insulin" with --Insulin-Like--.

In the right column, line 5, replace "G$_\alpha$C" with --G$_\alpha$ C--;

line 23, delete "Proc,"; and line 37, replace "lympoma" with --lymphoma--.

Col. 1, line 28, replace "Go" with --G$_\alpha$--;

Col. 1, line 46, replace "B-B-X-S" with --B-B-X-B--;

Col. 1, line 46, replace "S is" with --B is--;

Col. 3, line 3, replace "receptor" with --receptors--;

UNITED STATES PATENT AND TRADEMARK OFFICE
CERTIFICATE OF CORRECTION

PATENT NO.  : 5,559,209

DATED       : September 24, 1996

INVENTOR(S) : Ikuo Nishimoto

It is certified that error appears in the above-identified patent and that said Letters Patent is hereby corrected as shown below:

Col. 3, line 20, replace "((C)" with --(C)--;

Col. 4, line 66, replace "$ACG_\alpha$" with --$ACG_s$--;

Col. 5, line 44, "Materials and Methods" should be on a separate line, and "The in vitro assays described below" should start a new paragraph on the next line.

Col. 6, line 15, replace "BT", both occurrences, with --$B_T$--;

Col. 6, line 26, replace "(567)" with --(♦)--;

Col. 7, line 11, replace "GTPβS" with --$GTP_\tau S$--;

Col. 7, line 36, replace "GTPβS" with --$GTP_\tau S$--;

Col. 7, line 44, after "(1987)", insert --)--;

Col. 8, line 3, replace "≥" with --≤--;

Col. 8, line 58, underline "A" in "TAV";

Col. 8, line 60, underline "A" in "KAC";

Col. 8, line 62, replace "≥" with --≤--;

Col. 8, line 63, underline "A" in "AAV";

Col. 8, line 66, replace "IKNNLKDC" with --IK<u>A</u>NLKDC--;

Col. 9, line 6, underline "A" in "NAL";

Col. 9, line 34, replace "30° C." with --30°C--;

Col. 9, line 41, replace "was≈75%" with --was ≈75%--;

UNITED STATES PATENT AND TRADEMARK OFFICE
CERTIFICATE OF CORRECTION

PATENT NO. : 5,559,209

DATED : September 24, 1996

INVENTOR(S) : Ikuo Nishimoto

It is certified that error appears in the above-identified patent and that said Letters Patent is hereby corrected as shown below:

Col. 10, line 6, replace "Of" with --of--;

Col. 10, line 53, before ")" delete the period;

Col. 10, line 64, after "increase", delete ",";

Col. 11, line 56, replace "2xconcentrated" with --2X concentrated--;

Col. 11, line 61, after "C", delete the period;

Col. 12, line 40, replace " [$^3$H] incorporation" with --[$^3$H] incorporation--;

Col. 12, line 54, replace "mMACG$_q$" with --mM ACG$_q$--;

Col. 12, line 54, replace "mMACG$_{i2}$" with --mM ACG$_{i2}$--;

Col. 12, line 59, replace "With" with --with--; and

Col. 13, line 66, replace "are-within" with --are within--.

Signed and Sealed this

Fifteenth Day of September, 1998

Attest:

BRUCE LEHMAN

Attesting Officer

Commissioner of Patents and Trademarks